(12) United States Patent
Hughes et al.

(10) Patent No.: US 8,475,819 B2
(45) Date of Patent: Jul. 2, 2013

(54) CYANO ANTHRANILAMIDE INSECTICIDES

(75) Inventors: Kenneth Andrew Hughes, Rising Sun, MD (US); George Philip Lahm, Wilmington, DE (US); Thomas Paul Selby, Hockessin, DE (US); Thomas Martin Stevenson, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/971,287

(22) Filed: Dec. 17, 2010

(65) Prior Publication Data

US 2011/0319452 A1    Dec. 29, 2011

Related U.S. Application Data

(62) Division of application No. 11/811,105, filed on Jun. 8, 2007, now Pat. No. 7,875,634, which is a division of application No. 10/540,966, filed as application No. PCT/US2004/003568 on Jan. 21, 2004, now Pat. No. 7,247,647.

(60) Provisional application No. 60/443,256, filed on Jan. 28, 2003.

(51) Int. Cl.
    *A01N 25/02* (2006.01)
(52) U.S. Cl.
    USPC .......................................... 424/405; 514/341
(58) Field of Classification Search
    USPC ....................................................... 514/341
    See application file for complete search history.

(56) References Cited

U.S. PATENT DOCUMENTS

| 4,833,158 | A | * | 5/1989 | Twydell et al. ............... 514/616 |
|---|---|---|---|---|
| 5,998,424 | A | | 12/1999 | Galemmo et al. |
| 6,020,357 | A | | 2/2000 | Pinto et al. |
| 6,403,620 | B1 | | 6/2002 | Galemmo et al. |
| 6,548,512 | B1 | | 4/2003 | Pinto et al. |
| 6,602,895 | B2 | | 8/2003 | Galemmo et al. |
| 6,747,047 | B2 | | 6/2004 | Lahm et al. |
| 7,442,799 | B2 | | 10/2008 | Annis |
| 7,560,564 | B2 | | 7/2009 | Annis et al. |
| 2004/0102324 | A1 | | 5/2004 | Annis et al. |
| 2004/0110777 | A1 | | 6/2004 | Annis et al. |
| 2004/0138450 | A1 | | 7/2004 | Clark |
| 2004/0142984 | A1 | | 7/2004 | Lahm et al. |
| 2004/0171649 | A1 | | 9/2004 | Annis et al. |
| 2004/0192731 | A1 | | 9/2004 | Finkelstein et al. |
| 2004/0198984 | A1 | | 10/2004 | Lahm et al. |
| 2004/0198987 | A1 | | 10/2004 | Freudenberger et al. |
| 2004/0209923 | A1 | | 10/2004 | Berger et al. |
| 2004/0259913 | A1 | | 12/2004 | Clark |
| 2005/0075372 | A1 | | 4/2005 | Lahm et al. |
| 2005/0124600 | A1 | | 6/2005 | Clark et al. |
| 2005/0147633 | A1 | | 7/2005 | Stevenson |
| 2005/0215785 | A1 | | 9/2005 | Taylor |
| 2005/0215798 | A1 | | 9/2005 | Annis |
| 2005/0245580 | A1 | | 11/2005 | Freudenberger et al. |
| 2006/0014808 | A1 | | 1/2006 | Hughes et al. |
| 2006/0052343 | A1 | | 3/2006 | Lahm et al. |
| 2006/0079561 | A1 | | 4/2006 | Lahm et al. |
| 2006/0241304 | A1 | | 10/2006 | Taylor |

(Continued)

FOREIGN PATENT DOCUMENTS

| EP | 991625 B1 | 6/2005 |
|---|---|---|
| EP | 946508 B1 | 9/2009 |

(Continued)

OTHER PUBLICATIONS

PCT Search Report for International Application No. PCT/US2004/003568 (From International Phase of Parent U.S. Appl. No. 10/540,966).

*Primary Examiner* — Neil Levy

(57) ABSTRACT

This invention provides compounds of Formula 1, N-oxides and suitable salts thereof

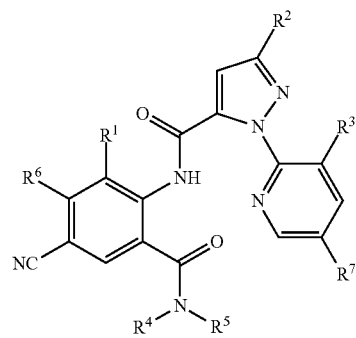

wherein
$R^1$ is Me, Cl, Br or F;
$R^2$ is F, Cl, Br, $C_1$-$C_4$ haloalkyl or $C_1$-$C_4$ haloalkoxy;
$R^3$ is F, Cl or Br;
$R^4$ is H; $C_1$-$C_4$ alkyl, $C_3$-$C_4$ alkenyl, $C_3$-$C_4$ alkynyl, $C_3$-$C_5$ cycloalkyl, or $C_4$-$C_6$ cycloalkylalkyl, each optionally substituted with one substituent selected from the group consisting of halogen, CN, SMe, S(O)Me, S(O)$_2$Me, and OMe;
$R^5$ is H or Me;
$R^6$ is H, F or Cl; and
$R^7$ is H, F or Cl.
Also disclosed are methods for controlling an invertebrate pest comprising contacting the invertebrate pest or its environment with a biologically effective amount of a compound of Formula 1, an N-oxide thereof or a suitable salt of the compound (e.g., as a composition described herein). This invention also pertains to a composition for controlling an invertebrate pest comprising a biologically effective amount of a compound of Formula 1, an N-oxide thereof or a suitable salt of the compound and at least one additional component selected from the group consisting of a surfactant, a solid diluent and a liquid diluent.

6 Claims, No Drawings

U.S. PATENT DOCUMENTS

| | | |
|---|---|---|
| 2007/0161797 A1 | 7/2007 | Shapiro |
| 2007/0184018 A1 | 8/2007 | Lahm et al. |
| 2008/0027046 A1 | 1/2008 | Annan et al. |
| 2008/0108821 A1 | 5/2008 | Annis |
| 2008/0275061 A1 | 11/2008 | Lahm et al. |
| 2008/0305093 A1 | 12/2008 | Gutsche et al. |
| 2009/0036686 A1 | 2/2009 | Annis |
| 2009/0104145 A1 | 4/2009 | Annan et al. |
| 2009/0133318 A1 | 5/2009 | Lahm et al. |

FOREIGN PATENT DOCUMENTS

| | | |
|---|---|---|
| WO | 98/28269 | 7/1998 |
| WO | 98/57937 | 12/1998 |
| WO | 01/70671 | 9/2001 |
| WO | 03/015518 | 2/2003 |
| WO | 03/015519 | 2/2003 |
| WO | 03/016284 | 2/2003 |
| WO | 03/024222 | 3/2003 |
| WO | 03/106427 | 12/2003 |
| WO | 2004/033468 | 4/2004 |
| WO | 2004/046129 | 6/2004 |
| WO | 2004/087689 | 10/2004 |
| WO | 2004/111030 | 12/2004 |
| WO | 2005/070888 | 8/2005 |

\* cited by examiner

CYANO ANTHRANILAMIDE INSECTICIDES

CROSS-REFERENCES TO RELATED APPLICATIONS

This application is a division of U.S. application Ser. No. 11/811,105, filed Jun. 8, 2007, now U.S. Pat. No. 7,875,634, which is a division of U.S. application Ser. No. 10/540,966, filed on Jun. 29, 2005, now U.S. Pat. No. 7,247,647, which is a 371 national stage entry of PCT/US2004/003568, internationally filed on Jan. 21, 2004, which claims priority from U.S. Provisional Application No. 60/443,256, filed Jan. 28, 2003.

FIELD OF THE INVENTION

This invention relates to certain anthranilamides, their N-oxides, salts and compositions suitable for agronomic and nonagronomic uses, including those uses listed below, and a method of their use for controlling invertebrate pests in both agronomic and nonagronomic environments.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

WO 01/070671 discloses N-acyl anthranilic acid derivatives of Formula i as arthropodicides

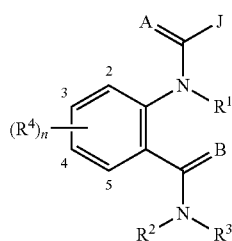

wherein, inter alia, A and B are independently O or S; J is an optionally substituted phenyl ring, 5- or 6-membered heteroaromatic ring, naphthyl ring system or an aromatic 8-, 9- or 10-membered fused heterobicyclic ring system; $R^1$ and $R^3$ are independently H or optionally substituted $C_1$-$C_6$ alkyl; $R^2$ is H or $C_1$-$C_6$ alkyl; each $R^4$ is independently H, $C_1$-$C_6$ alkyl, $C_1$-$C_6$ haloalkyl, halogen or CN; and n is 1 to 4.

SUMMARY OF THE INVENTION

This invention pertains to compounds of Formula 1, their N-oxides or salts thereof

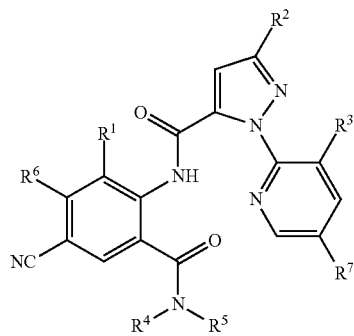

wherein
- $R^1$ is Me, Cl, Br or F;
- $R^2$ is F, Cl, Br, $C_1$-$C_4$ haloalkyl or $C_1$-$C_4$ haloalkoxy;
- $R^3$ is F, Cl or Br;
- $R^4$ is H; $C_1$-$C_4$ alkyl, $C_3$-$C_4$ alkenyl, $C_3$-$C_4$ alkynyl, $C_3$-$C_5$ cycloalkyl, or $C_4$-$C_6$ cycloalkylalkyl, each optionally substituted with one substituent selected from the group consisting of halogen, CN, SMe, S(O)Me, S(O)$_7$Me, and OMe;
- $R^5$ is H or Me;
- $R^6$ is H, F or Cl; and
- $R^7$ is H, F or Cl.

This invention also pertains to a composition for controlling an invertebrate pest comprising a biologically effective amount of a compound of Formula 1 and at least one additional component selected from the group consisting of a surfactant, a solid diluent and liquid diluent and optionally an effective amount of at least one additional biologically active compound or agent.

This invention also pertains to a method for controlling an invertebrate pest comprising contacting the invertebrate pest or its environment with a biologically effective amount of a compound of Formula 1 (e.g., as a composition described herein). This invention also relates to a method for controlling an invertebrate pest comprising contacting the invertebrate pest or its environment with a biologically effective amount of a composition comprising a biologically effective amount of a compound of Formula 1 and at least one additional component selected from the group consisting of a surfactant, a solid diluent and a liquid diluent, said composition optionally further comprising an effective amount of a of at least one additional biologically active compound or agent.

This invention further pertains to a spray composition comprising a compound of Formula 1 and a propellant, and to a bait composition comprising a compound of Formula 1, one or more food materials, an optional attractant, and an optional humectant. This invention also pertains to a device for controlling an invertebrate pest comprising said bait composition and a housing adapted to receive the bait composition, wherein the housing has at least one opening sized to permit the invertebrate pest to pass through the opening so the invertebrate pest can gain access to the bait composition from a location outside the housing and wherein the housing is further adapted to be placed in or near a locus of potential or known activity for the invertebrate pest.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl isomers. The term "halogen", either alone or in compound words such as "haloalkoxy", includes fluorine, chlorine, bromine or iodine. Further, when used in compound words such as "haloalkyl", or "haloalkoxy", said alkyl or alkoxy may be partially or fully substituted with halogen atoms which may be the same or different. Examples of "haloalkyl" include $F_3C$, $ClCH_2$, $CF_3CH_2$ and $CF_3CCl_2$. Examples of "haloalkoxy" include $CF_3O$, $HCF_2O$, $CCl_3CH_2O$, $HCF_2CH_2CH_2O$ and $CF_3CH_2O$.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydroxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula 1, N-oxides and salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. In the compositions and methods of this invention, the salts of the compounds of the invention are preferably suitable for the agronomic and/or non-agronomic uses described herein.

Of note are compounds of Formula I wherein
   $R^4$ is H or $C_1$-$C_4$ alkyl optionally substituted with one substituent selected from the group consisting of CN, SMe and OMe;
   $R^5$ is H or Me;
   $R^6$ is H; and
   $R^7$ is H.
Preferred compounds for reasons of cost, ease of synthesis and/or biological efficacy are:

Preferred 1. Compounds of Formula 1 wherein
   $R^1$ is Me or Cl;
   $R^2$ is Cl, Br, $CF_3$, $OCF_2H$, $OCF_3$ or $OCH_2CF_3$; and
   $R^4$ is H, Me, Et, i-Pr, t-Bu, $CH_2CN$, $CH(Me)CH_2SMe$ or $C(Me)_2CH_2SMe$.
Preferred 2. Compounds of Preferred 1 wherein
   $R^2$ is Cl, Br, $CF_3$ or $OCH_2CF_3$;
   $R^4$ is H, Me, Et or i-Pr; and
   $R^5$ is H.
Of note are compounds of Preferred 1 and Preferred 2 wherein $R^6$ is H; and $R^7$ is H.

The preferred compositions of the present invention are those, which comprise the above preferred compounds. The preferred methods of use are those involving the above-preferred compounds.

The compounds of Formula 1 can be prepared by one or more of the following methods and variation as described in Schemes 1-20. The definitions of $R^1$, $R^2$, $R^3$, $R^4$, and $R^5$ in the compounds of Formulae 1-24 below are as defined above in the Summary of the Invention unless indicated otherwise.

Compounds of Formula 1 can be prepared by the reaction of benzoxazinones of Formula 2 with an amine of Formula $HNR^4R^5$ as outlined in Scheme 1. This reaction can be run neat or in a variety of suitable solvents including tetrahydrofuran, diethyl ether, dioxane, toluene, dichloromethane or chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and Medicinal Chemistry* 2000, 8, 2095-2103 and references cited within. See also G. M. Coppola, *J. Heterocyclic Chemistry* 1999, 36, 563-588.

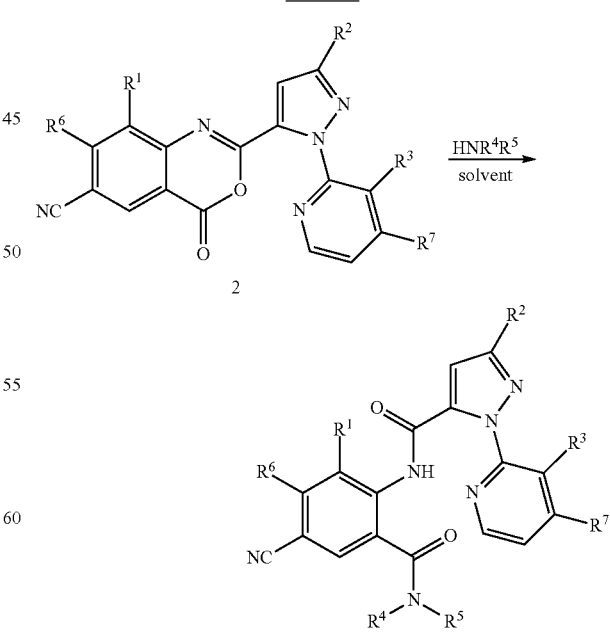

Scheme 1

Compounds of Formula 1 can also be prepared from haloanthranilic diamides of Formula 3 (wherein X is halogen, preferably iodine or bromine) by the coupling method shown in Scheme 2. Reaction of a compound of Formula 3 with a metal cyanide (e.g. cuprous cyanide, zinc cyanide, or potassium cyanide), optionally with or without a suitable palladium catalyst [e.g. tetrakis(triphenylphosphine)palladium(0) or dichlorobis(triphenylphosphine) palladium(II)] and optionally with or without a metal halide (e.g. cuprous iodide, zinc iodide, or potassium iodide) in a suitable solvent such as acetonitrile, N,N-dimethylformamide or N-methylpyrrolidinone, optionally at temperatures ranging from room temperature to the reflux temperature of the solvent, affords compounds of Formula 1. The suitable solvent can also be tetrahydrofuran or dioxane when palladium catalyst is used in the coupling reaction.

without a palladium catalyst and optionally with or without a metal halide present) affords a compound of Formula 2.

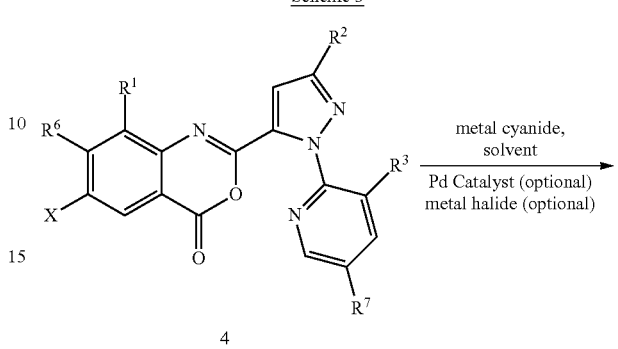

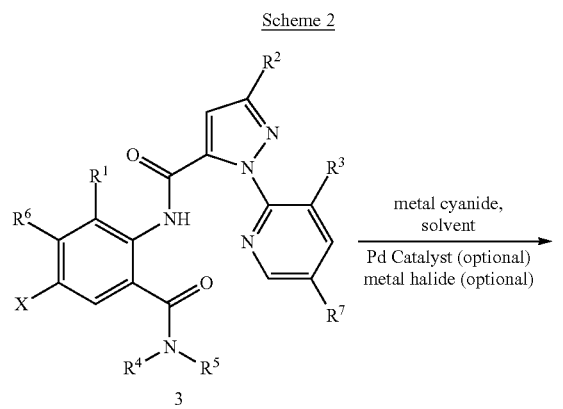

Cyanobenzoxazinones of Formula 2 can also be prepared by the method detailed in Scheme 4 via coupling of a pyrazole carboxylic acid of Formula 5 with a cyanoanthranilic acid of Formula 6. This reaction involves sequential addition of methanesulfonyl chloride in the presence of a tertiary amine such as triethylamine or pyridine to a pyrazole carboxylic acid of Formula 5, followed by the addition of cyanoanthranilic acid of Formula 6, followed by a second addition of tertiary amine and methanesulfonyl chloride.

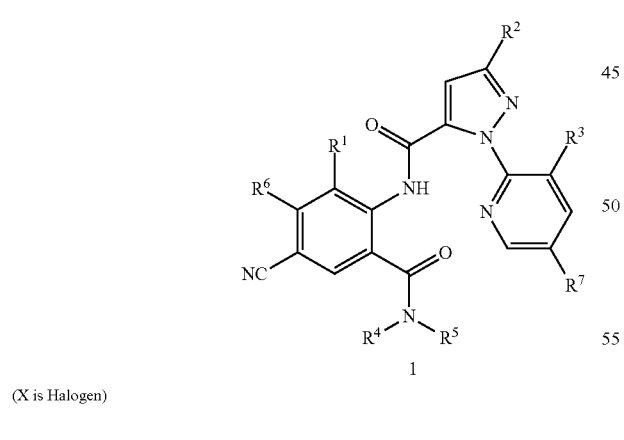

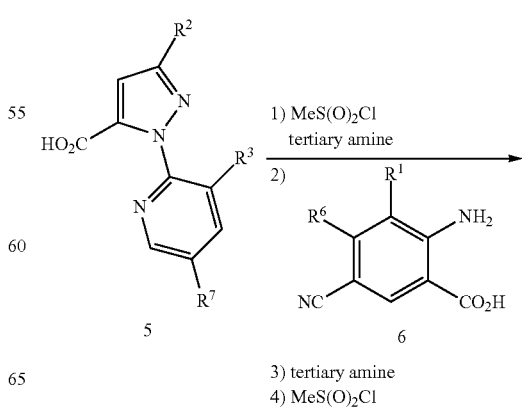

Cyanobenzoxazinones of Formula 2 can be prepared by the method outlined in Scheme 3. Reaction of a halobenzoxazinone of Formula 4 (wherein X is halogen, preferably iodine or bromine) with a metal cyanide using a similar coupling method as described above for Scheme 2 (optionally with or

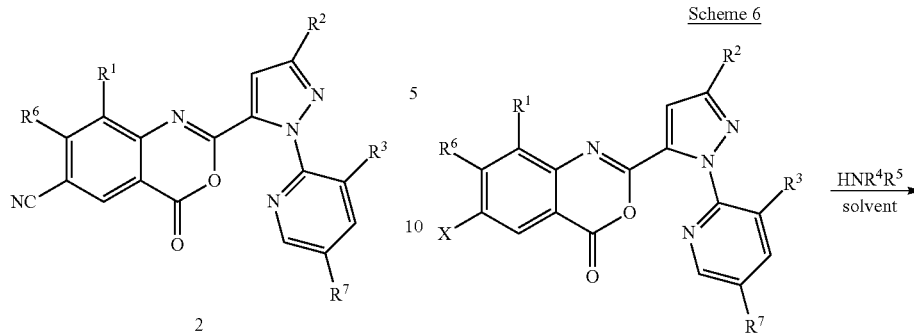

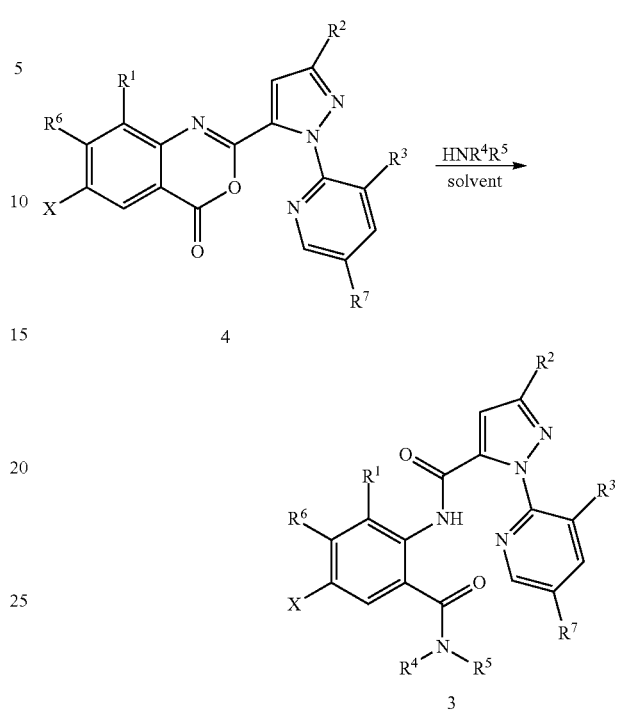

3

X is halogen

As shown in Scheme 7, halobenzoxazinones of Formula 4 (wherein X is halogen) can be prepared via direct coupling of a pyridylpyrazole carboxylic acid of Formula 5 with a haloanthranilic acid of Formula 9 (wherein X is halogen) by a similar method as described above for Scheme 4. This reaction involves sequential addition of methanesulfonyl chloride in the presence of a tertiary amine such as triethylamine or pyridine to a pyrazolecarboxylic acid of Formula 5, followed by the addition of a haloanthranilic acid of Formula 9, followed by a second addition of tertiary amine and methanesulfonyl chloride. This method generally affords good yields of the benzoxazinone.

Scheme 5 depicts another method for preparing benzoxazinones of Formula 2 involving coupling an isatoic anhydride of Formula 7 with a pyrazole acid chloride of Formula 8. Solvents such as pyridine or pyridine/acetonitrile are suitable for this reaction. The acid chlorides of Formula 8 are available from the corresponding acids of Formula 5 by known methods such as chlorination with thionyl chloride or oxalyl chloride.

Scheme 5

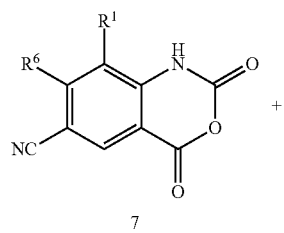

7

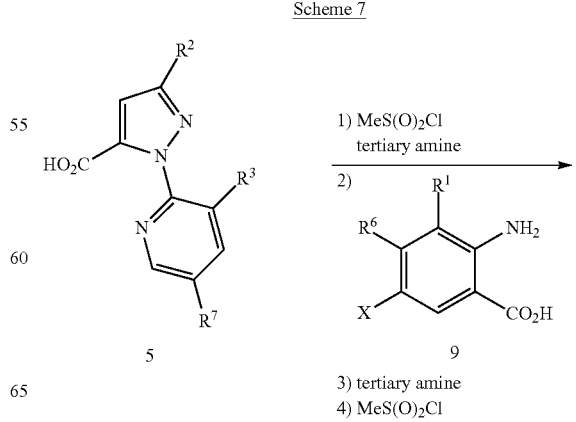

Scheme 7

As shown in Scheme 6, haloanthranilic diamides of Formula 3 can be prepared by the reaction of benzoxazinones of Formula 4, wherein X is halogen, with an amine of Formula $HNR^4R^5$ using a similar method as described above for Scheme 1. Conditions for this reaction are similar to those specified in Scheme 1.

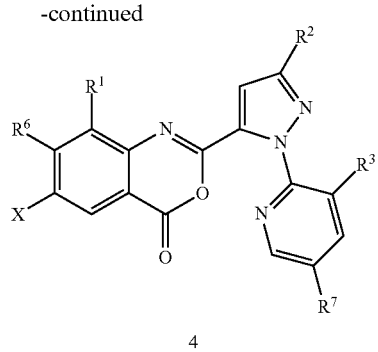

X is halogen

As shown in Scheme 8, a halobenzoxazinone of Formula 4 can also be prepared via coupling an isatoic anhydride of Formula 10 (wherein X is halogen) with a pyrazole acid chloride of Formula 8 by a similar method as described above for Scheme 5.

Scheme 8

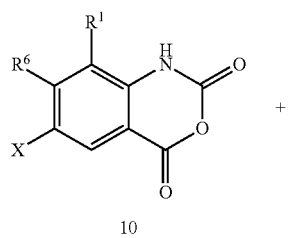

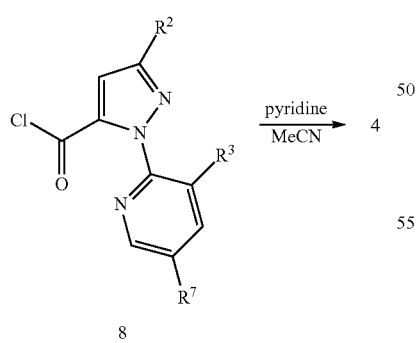

X is halogen

Cyanoanthranilic acids of Formula 6 can be prepared from haloanthranilic acids of Formula 9 as outlined in Scheme 9.

Reaction of a haloanthranilic acid of Formula 9 (wherein X is halogen) with a metal cyanide using the same coupling procedure described above for Scheme 2 (optionally with or without a palladium catalyst and optionally with or without a metal halide present) affords a compound of Formula 6.

Scheme 9

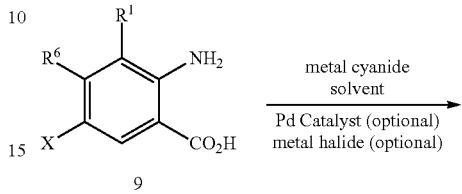

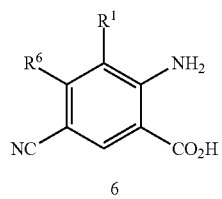

X is halogen

As illustrated in Scheme 10, cyanoisatoic anhydrides of Formula 7 can be prepared from cyanoanthranilic acids of Formula 6 by reaction with phosgene (or a phosgene equivalent such as triphosgene) or an alkyl chloroformate (e.g. methyl chloroformate) in a suitable solvent such as toluene or tetrahydrofuran.

Scheme 10

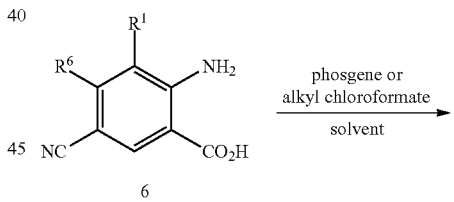

As shown in Scheme 11, haloanthranilic acids of Formula 9 can be prepared by direct halogenation of an unsubstituted anthranilic acid of Formula 11 with N-chlorosuccinimide (NCS), N-bromosuccinimide (NBS) or N-iodosuccinimide (NIS) respectively in solvents such as N,N-dimethylformamide (DMF) to produce the corresponding halogen-substituted acid of Formula 9.

Scheme 11

As illustrated in Scheme 12, haloisatoic anhydrides of Formula 10 can be prepared from haloanthranilic acids of Formula 9 by reaction with phosgene (or a phosgene equivalent such as triphosgene) or an alkyl chloroformate, e.g. methyl chloroformate, in a suitable solvent such as toluene or tetrahydrofuran.

Scheme 12

Pyridylpyrazole carboxylic acids of Formula 5 can be prepared by the method outlined in Scheme 13. Reaction of pyrazole 12 with a 2-halopyridine of Formula 13 in the presence of a suitable base such as potassium carbonate in a solvent such as N,N-dimethylformamide or acetonitrile affords good yields of the 1-pyridylpyrazole 14 with good specificity for the desired regiochemistry. Metallation of 14 with lithium diisopropylamide (LDA) followed by quenching of the lithium salt with carbon dioxide affords the pyrazole carboxylic acid of Formula 5.

Scheme 13

The starting pyrazoles 12 wherein $R^2$ is $CF_3$, Cl or Br are known compounds. Pyrazole 12 wherein $R^2$ is $CF_3$ can be prepared by literature procedures (*J. Fluorine Chem.* 1991, 53(1), 61-70). Pyrazoles 12 wherein $R^2$ is Cl or Br can also be prepared by literature procedures (H. Reimlinger and A. Van Overstraeten, *Chem. Ber.* 1966, 99(10), 3350-7). A useful alternative method for the preparation of 12 wherein $R^2$ is Cl or Br is depicted in Scheme 14. Metallation of the sulfamoyl pyrazole 15 with n-butyllithium followed by direct halogenation of the anion with either hexachloroethane (for $R^2$ being Cl) or 1,2-dibromo-tetrachloroethane (for $R^2$ being Br) affords the halogenated derivatives 16 (where $R^2$ is Cl or Br). Removal of the sulfamoyl group with trifluoroacetic acid (TFA) at room temperature proceeds cleanly and in good yield to afford the pyrazoles 12 wherein $R^2$ is Cl or Br respectively.

Scheme 14

As an alternative to the method illustrated in Scheme 13, pyrazolecarboxylic acids of Formula 5 wherein $R^2$ is $CF_3$ can also be prepared by the method outlined in Scheme 15. Reaction of a compound of Formula 17 (wherein $R^8$ is $C_1$-$C_4$ alkyl) with a suitable base in a suitable organic solvent affords the cyclized product of Formula 18 after neutralization with an acid such as acetic acid.

Scheme 15

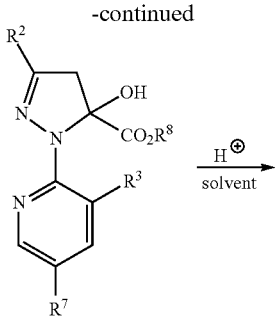

18

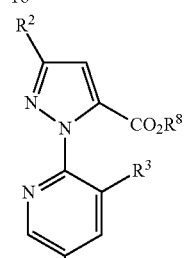

19

The suitable base can be for example but not limited to, sodium hydride, potassium t-butoxide, dimsyl sodium (CH$_3$S(O)CH$_2$—Na$^+$), alkali metal (such as lithium, sodium or potassium) carbonates or hydroxides, tetraalkyl (such as methyl, ethyl or butyl)ammonium fluorides or hydroxides, or 2-tert-butylimino-2-diethylamino-1,3-dimethyl-perhydro-1,3,2-diazaphosphonine. The suitable organic solvent can be, for example but not limited to, acetone, acetonitrile, tetrahydrofuran, dichloromethane, dimethylsulfoxide, or N,N-dimethylformamide. The cyclization reaction is usually conducted in a temperature range from about 0 to 120° C. The effects of solvent, base, temperature and addition time are all interdependent, and choice of reaction conditions is important to minimize the formation of byproducts. A preferred base is tetrabutylammonimm fluoride.

Dehydration of the compound of Formula 18 to give the compound of Formula 19, followed by hydrolysis of the carboxylic ester function to carboxylic acid, affords the compound of Formula 5. The dehydration is accomplished by treatment with a catalytic amount of a suitable acid. This catalytic acid can be, for example but not limited to, sulfuric acid. The reaction is generally conducted using an organic solvent. As one skilled in the art will realize, dehydration reactions may be conducted in a wide variety of solvents, e.g. acetic acid, in a temperature range generally between about 0 and 200° C., more preferably between about 0 and 100° C. Carboxylic esters of Formula 19 can be converted to carboxylic acids of Formula 5 by numerous methods including nucleophilic cleavage under anhydrous conditions or hydrolytic methods involving the use of either acids or bases (see T. W. Greene and P. G. M. Wuts, *Protective Groups in Organic Synthesis,* 2nd ed., John Wiley & Sons, Inc., New York, 1991, pp. 224-269 for a review of methods). For the method of Scheme 15, base-catalyzed hydrolytic methods are preferred. Suitable bases include alkali metal (such as lithium, sodium or potassium) hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 5.

Compounds of Formula 17 wherein R$^2$ is CF$_3$ can be prepared by the method outlined in Scheme 16. Treatment of a hydrazine compound of Formula 20 with a ketone of Formula CH$_3$COR$^2$ in a solvent such as water, methanol or acetic acid gives the hydrazone of Formula 21.

Scheme 16

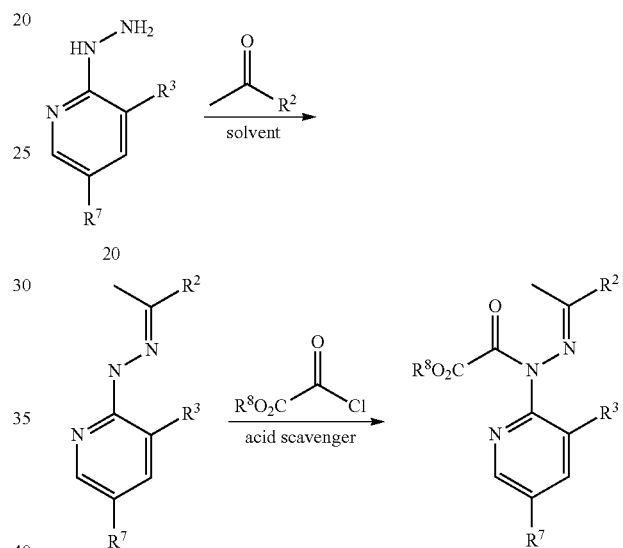

wherin R$^2$ is CF$_3$ and R$^8$ is C$_1$-C$_4$ alkyl

One skilled in the art will recognize that this reaction may require catalysis by an optional acid and may also require elevated temperatures depending on the molecular substitution pattern of the hydrazone of Formula 21. Reaction of the hydrazone of Formula 21 with an alkyl chlorooxalate in a suitable organic solvent such as, for example but not limited to, dichloromethane or tetrahydrofuran in the presence of an acid scavenger such as triethylamine provides the compound of Formula 17. The reaction is usually conducted at a temperature between about 0 and 100° C. Hydrazine compounds of Formula 20 can be prepared by standard methods, such as by reaction of the corresponding halopyridine of Formula 13 with hydrazine.

As an alternative to the method illustrated in Scheme 13, pyrazolecarboxylic acids of Formula 5 wherein R$^2$ is Cl or Br can also be prepared by the method outlined in Scheme 17. Oxidation of the compound of Formula 22, optionally in the presence of acid, gives the compound of Formula 19, wherein R$^2$ is Cl or Br. Hydrolysis of the carboxylic ester function to the carboxylic acid provides the compound of Formula 5.

Scheme 17

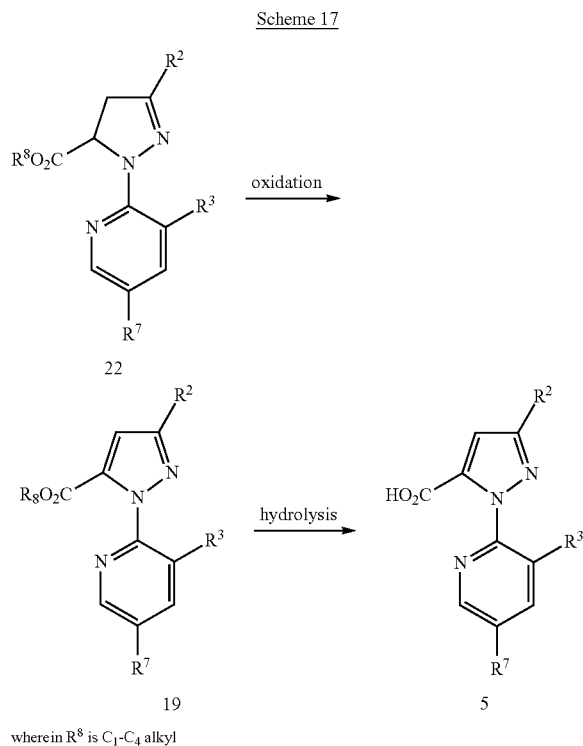

wherein R⁸ is $C_1$-$C_4$ alkyl

Scheme 18

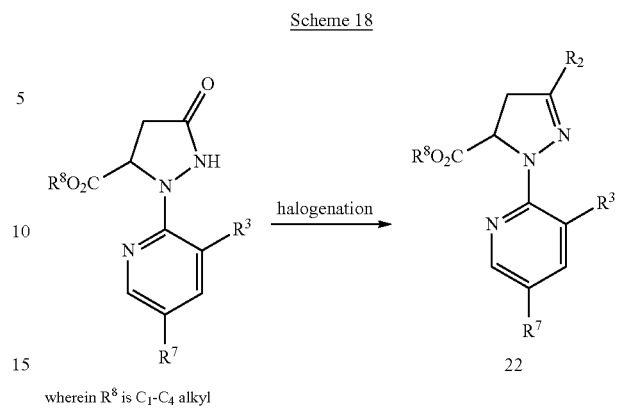

wherein R⁸ is $C_1$-$C_4$ alkyl

The oxidizing agent for converting a compound of Formula 22 to a compound of Formula 19 can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula 22 should be used, preferably between about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfuric acid, phosphoric acid and the like, and organic acids, such as acetic acid, benzoic acid and the like. One to five equivalents of acid can be used. The preferred oxidant is potassium persulfate and the oxidation is preferably carried out in the presence of sulfuric acid. The reaction can be carried out by mixing the compound of Formula 22 in the desired solvent and, if used, the acid. The oxidant can then be added at a convenient rate. The reaction temperature is typically varied from as low as about 0° C. up to the boiling point of the solvent in order to obtain a reasonable reaction time to complete the reaction. Methods suitable for converting the ester of Formula 19 to the carboxylic acid of Formula 5 are already described for Scheme 15.

Compounds of Formula 22, wherein R² is halogen and R⁸ is $C_1$-$C_4$ alkyl, can be prepared from the corresponding compounds of Formula 23 as shown in Scheme 18.

Treatment of a compound of Formula 23 with a halogenating reagent, usually in the presence of a solvent, affords the corresponding halo compound of Formula 22. Halogenating reagents that can be used include phosphorus oxyhalides, phosphorus trihalides, phosphorus pentahalides, thionyl chloride, dihalotrialkylphosphoranes, dihalodiphenylphosphoranes, oxalyl chloride and phosgene. Preferred are phosphorus oxyhalides and phosphorus pentahalides. To obtain complete conversion, at least 0.33 equivalents of phosphorus oxyhalide versus the compound of Formula 23 should be used, preferably between about 0.33 and 1.2 equivalents. To obtain complete conversion, at least 0.20 equivalents of phosphorus pentahalide versus the compound of Formula 23 should be used, preferably between about 0.20 and 1.0 equivalents. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula 23 in acetonitrile. The halogenating reagent is then added over a convenient time, and the mixture is then held at the desired temperature until the reaction is complete. The reaction temperature is typically between 20° C. and the boiling point of acetonitrile, and the reaction time is typically less than 2 hours. The reaction mass is then neutralized with an inorganic base, such as sodium bicarbonate, sodium hydroxide and the like, or an organic base, such as sodium acetate. The desired product of Formula 22 can be isolated by methods known to those skilled in the art, including crystallization, extraction and distillation.

Alternatively, compounds of Formula 22 wherein. R² is Br or Cl can be prepared by treating the corresponding compounds of Formula 22 wherein R² is a different halogen (e.g., Cl for making Formula 22 wherein R² is Br) or a sulfonate group such as p-toluenesulfonate, benzenesulfonate and methanesulfonate with hydrogen bromide or hydrogen chloride, respectively. By this method the R² halogen or sulfonate substituent on the compound of Formula 22 is replaced with Br or Cl from hydrogen bromide or hydrogen chloride, respectively. The reaction is conducted in a suitable solvent such as dibromomethane, dichloromethane, acetic acid, ethyl acetate or acetonitrile. The reaction can be conducted at or near atmospheric pressure or above atmospheric pressure in a pressure vessel. The halogenating reagent can be added in the form of a gas to the reaction mixture containing the Formula 23 compound and solvent. When $R^2$ in the starting compound of Formula 22 is a halogen such as Cl, the reaction is preferably conducted in such a way that sparging or other suitable means removes the hydrogen halide generated from the reaction. Alternatively, the halogenating reagent can first be dissolved in an inert solvent in which it is highly soluble (such as acetic acid) before contacting the compound of Formula 23 either neat or in solution. The reaction can be conducted between about 0 and 100° C., most conveniently near ambient temperature (e.g., about 10 to 40° C.), and more preferably between about 20 and 30° C. Addition of a Lewis acid catalyst (such as aluminum tribromide for preparing Formula 22 wherein $R^2$ is Br) can facilitate the reaction. The product of Formula 22 is isolated by the usual methods known to those skilled in the art, including extraction, distillation and crystallization.

Starting compounds of Formula 22 wherein $R^2$ is a sulfonate group can be prepared from corresponding compounds of Formula 23 by standard methods such as treatment with a sulfonyl chloride (e.g., p-toluenesulfonyl chloride) and base such as a tertiary amine (e.g., triethylamine) in a suitable solvent such as dichloromethane.

As an alternative to the method illustrated in Scheme 13, pyrazolecarboxylic acids of Formula 5 wherein $R^2$ is haloalkoxy can also be prepared by the method outlined in Scheme 19. A compound of Formula 23 is oxidized to a compound of Formula 24. The reaction conditions for this oxidation are as described for the conversion of the compound of Formula 22 to the compound of Formula 19 in Scheme 17.

The intermediate of Formula 24 is then alkylated to form a compound of Formula 19 (wherein $R^2$ is haloalkoxy) by reaction with an appropriate haloalkylating agent such as a haloalkyl halide or sulfonate. The reaction is conducted in the presence of at least one equivalent of a base. Suitable bases include inorganic bases, such as alkali metal (such as lithium, sodium or potassium) carbonates, hydroxides and hydrides or organic bases, such as triethylamine, diisopropylethylamine and 1,8-diazabicyclo[5.4.0]undec-7-ene. The reaction is generally conducted in a solvent, which can comprise alcohols, such as methanol and ethanol, halogenated alkanes, such as dichloromethane, aromatic solvents, such as benzene, toluene and chlorobenzene, ethers, such as tetrahydrofuran, and polar aprotic solvents, such as such as acetonitrile, N,N-dimethylformamide, and the like. Alcohols and polar aprotic solvents are preferred for use with inorganic bases. Potassium carbonate as base and N,N-dimethylformamide or acetonitrile as solvent are preferred. The reaction is generally conducted between 0 and 150° C., most typically between ambient temperature and 100° C. The ester of Formula 24 can then be converted to the carboxylic acid of Formula 5 by the methods already described for the conversion of a compound of Formula 19 to a compound of Formula 5 in Scheme 15.

Compounds of Formula 23 can be prepared from compounds of Formula 20 as outlined in Scheme 20. In this method, a hydrazine compound of Formula 20 is allowed to react with a compound of Formula 25 (a fumarate ester or maleate ester or a mixture thereof can be used) in the presence of a base and a solvent.

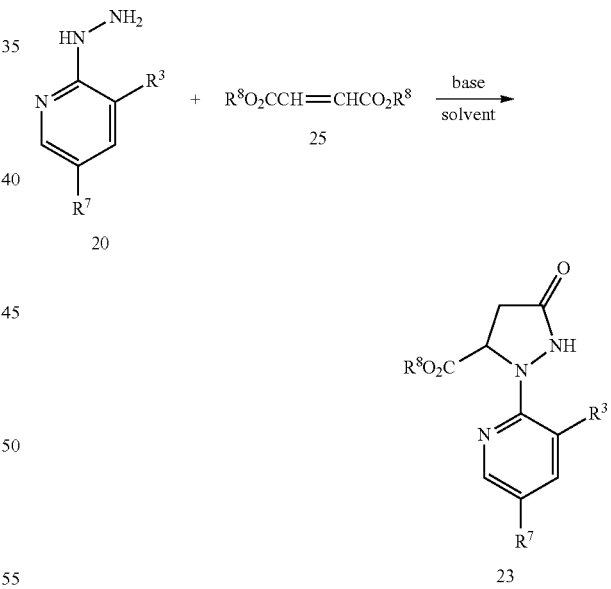

Scheme 20 wherein $R^8$ is $C_1$-$C_4$ alkyl

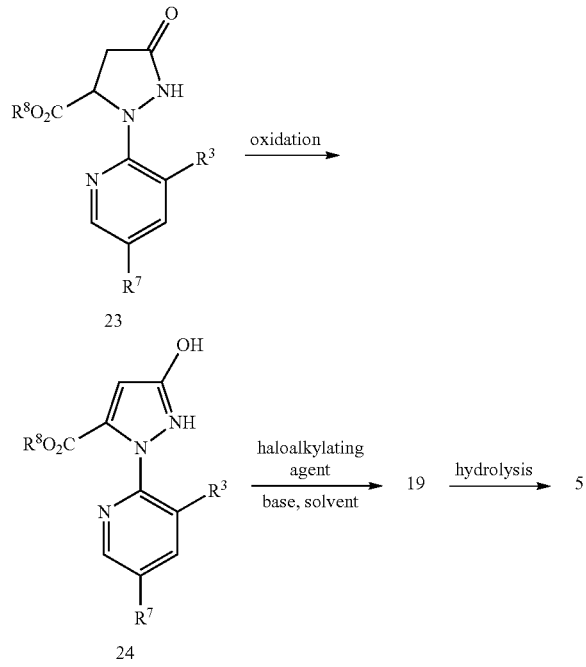

Scheme 19 wherein $R^2$ is haloalkoxy and $R^8$ is $C_1$-$C_4$ alkyl

The base used in Scheme 20 is typically a metal alkoxide salt, such as sodium methoxide, potassium methoxide, sodium ethoxide, potassium ethoxide, potassium tert-butoxide, lithium tert-butoxide, and the like. Polar protic and polar aprotic organic solvents can be used, such as alcohols, acetonitrile, tetrahydrofuran, N,N-dimethyl-formamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 20 and the base in the solvent. The mixture can be heated or cooled to a desired temperature and the compound of Formula 25 added over a period of time. Typically reaction temperatures are between 0° C. and the boiling point of the solvent used. The reaction may be conducted under greater than atmospheric pressure in order to increase the boiling point of the solvent. Temperatures between about 30 and 90° C. are generally preferred. The reaction can then be acidified by adding an organic acid, such as acetic acid and the like, or an inorganic acid, such as hydrochloric acid, sulfuric acid and the like. The desired product of Formula 23 can be isolated by methods known to those skilled in the art, such as crystallization, extraction or distillation.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, T. W. Greene and P. G. M. Wuts, *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet.

Example 1

Preparation of 1-(3-chloro-2-pyridinyl)-N-[4-cyano-2-methyl-6-(aminocarbonyl)phenyl]-3-(trifluoromethyl)-1H-pyrazole-5-carboxamide Step A: Preparation of 2-amino-3-methyl-5-iodobenzoic acid To a solution of 2-amino-3-methylbenzoic acid (Aldrich, 5 g, 33 mmol) in N,N-dimethylformamide (30 mL) was added N-iodosuccinimide (7.8 g, 34.7 mmol), and the reaction mixture was suspended in a 75° C. oil bath overnight. The heat was removed and the reaction mixture was then slowly poured into ice-water (100 mL) to precipitate a light grey solid. The solid was filtered and washed four times with water and then placed in a vacuum oven at 70° C. to dry overnight. The desired intermediate was isolated as a light grey solid (8.8 g).

$^1$H NMR (DMSO-$d_6$): δ 7.86 (d, 1H), 7.44 (d, 1H), 2.08 (s, 3H).

Step B: Preparation of 3-chloro-2-[3-(trifluoromethyl)-1H-pyrazol-1-yl]pyridine

To a mixture of 2,3-dichloropyridine (99.0 g, 0.67 mol) and 3-(trifluoromethyl)-pyrazole (83 g, 0.61 mol) in dry N,N-dimethylformamide (300 mL) was added potassium carbonate (166.0 g, 1.2 mol) and the reaction was then heated to 110-125° C. over 48 hours. The reaction was cooled to 100° C. and filtered through Celite® diatomaceous filter aid to remove solids. N,N-Dimethylformamide and excess dichloropyridine were removed by distillation at atmospheric pressure. Distillation of the product at reduced pressure (b.p. 139-141° C., 7 mm) afforded 113.4 g of the desired intermediate as a clear yellow oil.

$^1$H NMR (CDCl$_3$): δ 8.45 (d, 1H), 8.15 (s, 1H), 7.93 (d, 1H), 7.36 (t, 1H), 6.78 (s, 1H).

Step C: Preparation of 1-(3-chloro-2-pyridinyl)-3-(trifluoromethyl)-1H-pyrazole-5-carboxylic acid To a solution of 3-chloro-2-[3-(trifluoromethyl)-1H-pyrazol-1-yl]pyridine (i.e. the pyrazole product from Step B) (105.0 g, 425 mmol) in dry tetrahydrofuran (700 ml) at −75° C. was added via cannula a −30° C. solution of lithium diisopropylamide (425 mmol) in dry tetrahydrofuran (300 mL). The deep red solution was stirred for 15 minutes, after which time carbon dioxide was bubbled through at −63° C. until the solution became pale yellow and the exothermicity ceased. The reaction was stirred for an additional 20 minutes and then quenched with water (20 mL). The solvent was removed under reduced pressure, and the reaction mixture partitioned between ether and 0.5 N aqueous sodium hydroxide solution. The aqueous extracts were washed with ether (3×), filtered through Celite® diatomaceous filter aid to remove residual solids, and then acidified to a pH of approximately 4, at which point an orange oil fainted. The aqueous mixture was stirred vigorously and additional acid was added to lower the pH to 2.5-3. The orange oil congealed into a granular solid, which was filtered, washed successively with water and 1 N hydrochloric acid, and dried under vacuum at 50° C. to afford 130 g of the title product as an off-white solid. Product from another run following a similar procedure melted at 175-176° C.

$^1$H NMR (DMSO-$d_6$): δ 7.61 (s, 1H), 7.76 (dd, 1H), 8.31 (d, 1H), 8.60 (d, 1H).

Step D: Preparation of 2-[1-(3-chloro-2-pyridinyl)-3-(trifluoromethyl)-1H-pyrazol-5-yl]-6-iodo-8-methyl-4H-3,1-benzoxazin-4-one To a solution of methanesulfonyl chloride (2.91 mL, 37.74 mmol) in acetonitrile (50 mL) was added dropwise a mixture of 1-(3-chloro-2-pyridinyl)-3-(trifluoromethyl)-1H-pyrazole-5-carboxylic acid (i.e. the carboxylic acid product of Step C) (10.0 g, 34.31 mmol) and triethylamine (4.78 mL, 34.31 mmol) in acetonitrile (50 mL) at −5° C. The reaction temperature was then maintained at 0° C. throughout successive addition of reagents. After stirring for 20 minutes, 2-amino-3-methyl-5-iodobenzoic acid (i.e. the product from Step A) (9.51 g, 34.31 mmol) was added and stirring was continued for an additional 10 minutes. A solution of triethylamine (9.56 mL, 68.62 mmol) in acetonitrile (15 mL) was then added dropwise, and the reaction mixture was stirred 30 minutes, followed by the addition of methanesulfonyl chloride (2.91 mL, 37.74 mmol). The reaction mixture was then warmed to room temperature and stirred 2 hours. The solvent was evaporated under reduced pressure, and the residual solid was purified by chromatography on silica gel to afford 8.53 g of the title compound as a yellow solid.

$^1$H NMR (CDCl$_3$): δ 8.59 (dd, 1H), 8.35 (d, 1H), 7.97 (dd, 1H), 7.86 (d, 1H), 7.49 (m, 2H), 1.79 (s, 3H).

Step E: Preparation of 2-[1-(3-chloro-2-pyridinyl)-3-(trifluoromethyl)-1H-pyrazol-5-yl]-6-cyano-8-methyl-4H-3,1-benzoxazin-4-one To a solution of 2-[1-(3-chloro-2-pyridinyl)-3-(trifluoromethyl)-1H-pyrazol-5-yl]-6-iodo-8-methyl-4H-3,1-benzoxazin-4-one (i.e. the benzoxazinone product of Step D) (500 mg, 0.94 mmol) in tetrahydrofuran (10 mL) was added copper (I) iodide (180 mg, 0.094 mmol), tetrakis(triphenyphosphine) palladium(0) (5.4 mg, 0.047 mmol) and copper(I) cyanide (420 mg, 4.7 mmol) sequentially at room temperature. After heating the reaction mixture at reflux overnight, additional copper(I) cyanide (420 mg, 4.7 mmol), copper(I) iodide (107 mg, 0.56 mmol) and tetrakis(triphenylphosphine)palladium (0) (325 mg, 0.28 mmol) were added and the reflux was continued for 1 hour. The reaction mixture turned black in color, at which point thin layer chromatography on silica gel confirmed completion of the reaction. The reaction mixture was then diluted with ethyl acetate (20 mL) and filtered through Celite®, followed by washing three times with 10% aqueous sodium bicarbonate solution and once with brine. The organic extract was dried (MgSO$_4$) and concentrated under reduced pressure to afford 410 mg of the title compound as a crude yellow solid.

$^1$H NMR (CDCl$_3$): δ 8.59 (dd, 1H), 8.33 (d, 1H), 8.03 (dd, 1H), 7.95 (d, 1H), 7.56 (m, 2H), 1.88 (s, 3H).

Step F: Preparation of 1-(3-chloro-2-pyridinyl)-N-[4-cyano-2-methyl-6-(aminocarbonyl)phenyl]-3-(trifluoromethyl)-1H-pyrazole-5-carboxamide To a solution of 2-[1-(3-chloro-2-pyridinyl)-3-(trifluoromethyl)-1H-pyrazol-5-yl]-6-cyano-8-methyl-4H-3,1-benzoxazin-4-one (i.e. the cyanobenzoxazinone product of Step E) (200 mg, 0.46 mmol) in tetrahydrofuran (5 mL) was added dropwise ammonium hydroxide (0.5 mL, 12.8 mmol) at room temperature. The reaction mixture was then stirred for five minutes, at which point thin layer chromatography on silica gel confirmed completion of the reaction. The tetrahydrofuran solvent was evaporated under reduced pressure, and the residual solid was purified by chromatography on silica gel to afford 620 mg of the title compound, a compound of the present invention, as a solid melting at 200-202° C.

$^1$H NMR (CDCl$_3$): δ 10.65 (s, 1H), 8.43 (dd, 1H), 7.9 (dd, 1H), 7.67 (s, 1H), 7.63 (s, 1H), 7.45 (m, 1H), 7.25 (s, 1H), 6.21 (bs, 1H), 5.75 (bs, 1H), 2.26, (s, 3H).

Example 2

Preparation of 1-(3-chloro-2-pyridinyl)-N-[4-cyano-2-methyl-6-[(methylamino)carbonyl]phenyl]-3-(trifluoromethyl)-1H-pyrazole-5-carboxamide Step A: Preparation of 1-(3-chloro-2-pyridinyl)-N-[4-iodo-2-methyl-6-[(methylamino)carbonyl]phenyl]-3-(trifluoromethyl)-1H-pyrazole-5-carboxamide To a solution of 2-[1-(3-chloro-2-pyridinyl)-3-(trifluoromethyl)-1H-pyrazol-5-yl]-6-iodo-8-methyl-4H-3,1-benzoxazin-4-one (i.e. the benzoxazinone product of Example 1, Step D) (500 mg, 0.94 mmol) in tetrahydrofuran (15 mL) was added dropwise methylamine (2.0 M solution in THF, 1.4 mL, 2.8 mmol) and the reaction mixture was stirred for 3 hours, at which point thin layer chromatography on silica: gel confirmed completion of the reaction. The tetrahydrofuran solvent was evaporated under reduced pressure and the residual solid was purified by chromatography on silica gel to afford 400 mg of the title compound as a yellow solid.

$^1$H NMR (CDCl$_3$): δ 10.25 (s, 1H), 8.45 (dd, 1H), 7.85 (dd, 1H), 7.55 (s, 1H), 7.50 (s, 1H), 7.46 (s, 1H), 7.40 (m, 1H), 6.15 (d, 1H), 2.93 (d, 3H), 2.12 (s, 3H).

Step B: Preparation of 1-(3-chloro-2-pyridinyl)-N-[4-cyano-2-methyl-6-[(methylamino)carbonyl]phenyl]-3-(trifluoromethyl)-1H-pyrazole-5-carboxamide To a solution of 1-(3-chloro-2-pyridinyl)-N-[4-iodo-2-methyl-6-[(methylamino)carbonyl]phenyl]-3-(trifluoromethyl)-1H-pyrazole-5-carboxamide (i.e. the diamide product of Step A) (410 mg, 0.72 mmol) in tetrahydrofuran (8 mL) was added copper(I) iodide (24 mg, 0.126 mmol), tetrakis (triphenylphosphine)palladium(0) (70 mg, 0.060 mmol) and copper(I) cyanide (640 mg, 7.2 mmol) sequentially at room temperature. The reaction mixture was heated at reflux for 4.5 hours. Thin layer chromatography on silica gel confirmed completion of the reaction. The reaction mixture was then diluted with ethyl acetate (20 mL) and filtered through Celite®, followed by washing three times with 10% aqueous sodium bicarbonate solution and once with brine. The organic extract was dried (MgSO$_4$) and concentrated under reduced pressure and the residual solid was purified by chromatography on silica gel to afford 114 mg of the title compound, a compound of the present invention, as a white solid, melting at 214-216° C.

$^1$H NMR (CDCl$_3$): δ 10.70 (s, 1H), 8.46 (dd, 1H), 7.87 (dd, 1H), 7.57 (s, 2H), 7.45 (m, 1H), 7.31 (s, 1H), 6.35 (d, 1H), 2.98 (d, 3H), 2.24 (s, 3H),

Example 3

Preparation of 3-chloro-1-(3-chloro-2-pyridinyl)-N-[4-cyano-2-methyl-6-[(methylamino)carbonyl]phenyl]-1H-pyrazole-5-carboxamide Step A: Preparation of 3-chloro-N,N-dimethyl-1H-pyrazole-1-sulfonamide To a solution of N-dimethylsulfamoylpyrazole (188.0 g, 1.07 mol) in dry tetrahydrofuran (1500 mL) at −78° C. was added dropwise a solution of 2.5 M n-butyl-lithium (472, mL, 1.18 mol) in hexane while maintaining the temperature below −65° C. Upon completion of the addition the reaction mixture was maintained at −78° C. for an additional 45 minutes, after which time a solution of hexachloroethane (279 g, 1.18 mol) in tetrahydrofuran (120 mL) was added dropwise. The reaction mixture was maintained for an hour at −78° C., warmed to −20° C. and then quenched with water (1 L). The reaction mixture was extracted with methylene chloride (4×500 mL); the organic extracts were dried over magnesium sulfate and concentrated. The crude product was further purified by chromatography on silica gel using methylene chloride as eluent to afford 160 g of the title product compound as a yellow oil.

$^1$H NMR (CDCl$_3$): δ 7.61 (s, 1H), 6.33 (s, 1H), 3.07 (d, 6H).

Step B: Preparation of 3-chloropyrazole

To trifluoroacetic acid (290 mL) was added dropwise 3-chloro-N,N-dimethyl-1H-pyrazole-1-sulfonamide (i.e. the chloropyrazole product of Step A) (160 g), and the reaction mixture was stirred at room temperature for 1.5 hrs and then concentrated at reduced pressure. The residue was taken up in hexane, insoluble solids were filtered off, and the hexane was concentrated to afford the crude product as an oil. The crude product was further purified by chromatography on silica gel using ether/hexane (40:60) as eluent to afford 64.44 g of the title product as a yellow oil.

$^1$H NMR (CDCl$_3$): δ 6.39 (s, 1H), 7.66 (s, 1H), 9.6 (br s, 1H).

Step C: Preparation of
3-chloro-2-(3-chloro-1H-pyrazol-1-yl)pyridine

To a mixture of 2,3-dichloropyridine (92.60 g, 0.629 mol) and 3-chloropyrazole (i.e. the product of Step B) (64.44 g, 0.629 mol) in N,N-dimethylformamide (400 mL) was added potassium carbonate (147.78 g, 1.06 mol), and the reaction mixture was then heated to 100° C. for 36 hours. The reaction mixture was cooled to room temperature and slowly poured into ice water. The precipitated solids were filtered and washed with water. The solid filter cake was taken up in ethyl acetate, dried over magnesium sulfate and concentrated. The crude solid was chromatographed on silica gel using 20% ethyl acetate/hexane as eluent to afford 39.75 g of the title product as a white solid.

$^1$H NMR (CDCl$_3$): δ 6.43 (s, 1H), 7.26 (m, 1H), 7.90 (d, 1H), 8.09 (s, 1H), 8.41 (d, 1H).

Step D: Preparation of 3-chloro-1-(3-chloro-2-pyridinyl)-1H-pyrazole-5-carboxylic acid To a solution of 3-chloro-2-(3-chloro-1H-pyrazol-1-yl)pyridine (i.e. the pyrazole product of Step C) (39.75 g, 186 mmol) in dry tetrahydrofuran (400 mL) at −78° C. was added dropwise a solution of 2.0 M diisopropylamide (93 mL, 186 mmol) in tetrahydrofuran. Carbon dioxide was bubbled through the amber solution for 1.4 minutes, after which time the solution became pale brownish-yellow. The reaction was made basic with 1 N aqueous sodium hydroxide solution and extracted with ether (2×500 mL). The aqueous extracts were acidified with 6 N hydrochloric acid followed by extraction with ethyl acetate (3×500 mL). The ethyl acetate extracts were dried over magnesium sulfate and concentrated to afford 42.96 g of the title product as an off-white solid. Product from another run following the same procedure melted at 198-199° C.

$^1$H NMR (DMSO-d$_6$): δ 6.99 (s, 1H), 7.45 (m, 1H), 7.93 (d, 1H), 8.51 (d, 1H).

Step E: Preparation of 2-[3-chloro-1-(3-chloro-2-pyridin yl)-1H-pyrazol-5-yl]-6-iodo-8-methyl-4H-3,1-benzoxazin-4-one To a solution of methanesulfonyl chloride (0.63 mL, 8.13 mmol) in acetonitrile (10 mL) was added dropwise a mixture of 3-chloro-1-(3-chloro-2-pyridinyl)-1H-pyrazole-5-carboxylic acid (i.e. the carboxylic acid product of Step D) (2.0 g, 7.75 mmol) and triethylamine (1.08 ml, 7.75 mmol) in acetonitrile (5 mL) at 0° C. The reaction mixture was then stirred for 15 minutes at 0° C. Then, 2-amino-3-methyl-5-iodobenzoic acid (i.e. the product from Example 1, Step A) (2.14 g, 7.75 mmol) was added, and stirring was continued for an additional 5 minutes. A solution of triethylamine (2.17 mL, 15.15 mmol) in acetonitrile (5 mL) was then added dropwise while keeping the temperature below 5° C. The reaction mixture was stirred 40 minutes at 0° C., and then methanesulfonyl chloride (0.63 mL, 8.13 mmol) was added. The reaction mixture was then warmed to room temperature and stirred overnight. The reaction mixture was then diluted with water (50 mL), and extracted with ethyl acetate (3×50 mL). The combined ethyl acetate extracts were washed successively with 10% aqueous sodium bicarbonate (1×20 mL) and brine (1×20 mL), dried (MgSO$_4$) and concentrated to afford 3.18 g of the title product as a crude yellow solid.

$^1$H NMR (CDCl$_3$): δ 8.55 (dd, 1H), 8.33 (s, 1H), 7.95 (dd, 1H), 7.82 (d, 1H), 7.45 (m, 1H), 7.16 (s, 1H), 1.77 (s, 3H).

Step F: Preparation of 2-[3-chloro-1-(3-chloro-2-pyridinyl)-1H-pyrazol-5-yl]-6-cyano-8-methyl-4H-3,1-benzoxazin-4-one To a solution of 2-[3-chloro-1-(3-chloro-2-pyridinyl)-1H-pyrazol-5-yl]-6-iodo-8-methyl-4H-3,1-benzoxazin-4-one (i.e. the benzoxazinone product of Step E) (600 mg; 1.2 mmol) in tetrahydrofuran (15 mL) was added copper(I) iodide (137 mg, 0.72 mmol), tetrakis(triphenyphosphine)palladium(0) (416 mg, 0.36 mmol) and copper(I) cyanide (860 mg, 9.6 mmol) sequentially at room temperature. The reaction mixture was then heated at reflux overnight. The reaction turned black in color, at which point thin layer chromatography on silica gel confirmed completion of the reaction. The reaction was diluted with ethyl acetate (20 mL) and filtered through Celite®, followed by washing three times with 10% aqueous sodium bicarbonate solution and once with brine. The organic extract was dried (MgSO$_4$) and concentrated under reduced pressure to afford 397 mg of the title compound as a crude yellow solid.

$^1$H NMR (CDCl$_3$): δ 8.50 (q, 1H), 8.22 (d, 1H), 7.90 (dd, 1H), 7.67 (d, 1H), 7.45 (m, 1H), 7.15 (s, 1H), 1.79 (s, 3H).

Step G: Preparation of 3-chloro-1-(3-chloro-2-pyridinyl)-N-[4-cyano-2-methyl-6-(methylamino)carbonyl]phenyl]-1H-pyrazole-5-carboxamide To a solution of 2-[3-chloro-1-(3-chloro-2-pyridinyl)-1H-pyrazol-5-yl]-6-cyano-8-methyl-4H-3,1-benzoxazin-4-one (e.g. the cyanobenzoxazinone product of Step F) (100 mg, 0.25 mmol) in tetrahydrofuran (5 mL) was added dropwise methylamine (2.0 M solution in MT, 0.5 mL, 1.0 mmol) and the reaction mixture was stirred for 5 minutes, at which point thin layer chromatography on silica gel confirmed completion of the reaction. The tetrahydrofuran solvent was evaporated under reduced pressure, and the residual solid was purified by chromatography on silica gel to afford the title compound, a compound of the present invention, as a white solid (52 mg), which decomposed in the melting apparatus above 140° C.

$^1$H NMR (CDCl$_3$): δ 10.55 (s, 1H), 8.45 (dd, 1H), 7.85 (dd, 1H), 7.55 (d, 2H), 7.40 (m, 1H), 6.97 (d, 1H), 6.30 (d, 1H), 2.98 (d, 3H), 2.24 (d, 3H).

Example 4

Preparation of 3-chloro-1-(3-chloro-2-pyridinyl)-N-[4-cyano-2-methyl-6-(aminocarbonyl)phenyl]-1H-pyrazole-5-carboxamide To a solution of 2-[3-chloro-1-(3-chloro-2-pyridinyl)-1H-pyrazol-5-yl]-6-cyano-8-methyl-4H-3,1-benzoxazin-4-one (i.e. the cyano-benzoxazinone product of Example 3, Step F) (100 mg, 0.25 mmol) tetrahydrofuran (5 mL) was added dropwise ammonium hydroxide (0.5 mL, 12.8 mmol) at room temperature. The reaction mixture was then stirred for five minutes, at which point thin layer chromatography on silica gel confirmed completion of the reaction. The tetrahydrofuran solvent was evaporated under reduced pressure, and the residual solid was purified by chromatography on silica gel to afford 55 mg of the title compound, a compound of the present invention, as a white solid that decomposes in the melting apparatus above 255° C.

$^1$H NMR (CDCl$_3$): δ 10.50 (s, 1H), 8.45 (dd, 1H), 7.85 (dd, 1H), 7.66 (d, 1H), 7.61 (s, 1H), 7.41 (m, 1H), 6.95 (s, 1H), 6.25 (bs, 1H), 5.75 (bs, 1H), 2.52 (s, 3H).

Example 5

Preparation of 3-bromo-1-(3-chloro-2-pyridinyl)-N-[4-cyano-2-methyl-6-[(methylamino)carbonyl]phenyl]-1H-pyrazole-5-carboxamide Step A: Preparation of 3-bromo-N,N-dimethyl-1H-pyrazole-1-sulfonamide To a solution of N,N-dimethylsulfamoylpyrazole (44.0 g, 0.251 mol) in dry tetrahydrofuran (500 mL) at −78° C. was added dropwise a solution of n-butyllithium (2.5 M in hexane, 105.5 mL, 0.264 mol) while maintaining the temperature below −60° C. A thick solid formed during the addition. Upon completion of the addition the reaction mixture was maintained for an additional 15 minutes, after which time a solution of 1,2-dibromo-tetrachloroethane (90 g, 0.276 mol) in tetrahydrofuran (150 mL) was added dropwise while maintaining the temperature below −70° C. The reaction mixture turned a clear orange; stirring was continued for an additional 15 minutes. The −78° C. bath was removed and the reaction was quenched with water (600 mL). The reaction mixture was extracted with methylene chloride (4×), and the organic extracts were dried over magnesium sulfate and concentrated. The crude product was further purified by chromatography on silica gel using methylene chloride-hexane (50:50) as eluent to afford 57.04 g of the title product as clear colorless oil.

$^1$H NMR (CDCl$_3$): δ 3.07 (d, 6H), 6.44 (m, 1H), 7.62 (m, 1H).

Step B: Preparation of 3-bromopyrazole

To trifluoroacetic acid (70 mL) was slowly added 3-bromo-N,N-dimethyl-1H-pyrazole-1-sulfonamide (i.e. the bromopyrazole product of Step A) (57.04 g). The reaction mixture was stirred at room temperature for 30 minutes and then concentrated at reduced pressure. The residue was taken up in hexane, insoluble solids were filtered off, and the hexane was evaporated to afford the crude product as an oil. The crude product was further purified by chromatography on silica gel using ethyl acetate/dichloromethane (10:90) as eluent to afford an oil. The oil was taken up in dichloromethane, neutralized with aqueous sodium bicarbonate solution, extracted with methylene chloride (3×), dried over magnesium sulfate and concentrated to afford 25.9 g of the title product as a white solid, m.p. 61-64° C.

$^1$H NMR (CDCl$_3$): δ 6.37 (d, 1H), 7.59 (d, 1H), 12.4 (br s, 1H).

Step C: Preparation of 2-(3-bromo-1H-pyrazol-1-yl)-3-chloropyridine

To a mixture of 2,3-dichloropyridine (27.4 g, 185 mmol) and 3-bromopyrazole (i.e. the product of Step B) (25.4 g, 176 mmol) in dry N,N-dimethylformamide (88 mL) was added potassium carbonate (48.6 g, 352 mmol), and the reaction mixture was heated to 125° C. for 18 hours. The reaction mixture was cooled to room temperature and poured into ice water (800 mL). A precipitate formed. The precipitated solids were stirred for 1.5 h, filtered and washed with water (2×100 mL). The solid filter cake was taken up in methylene chloride and washed sequentially with water, 1N hydrochloric acid, saturated aqueous sodium bicarbonate solution, and brine. The organic extracts were then dried over magnesium sulfate and concentrated to afford 39.9 g of a pink solid. The crude solid was suspended in hexane and stirred vigorously for 1 hr. The solids were filtered, washed with hexane and dried to afford the title product as an off-white powder (30.4 g) determined to be >94% pure by NMR. This material was used without further purification in Step D.

$^1$H NMR (CDCl$_3$): δ 6.52 (s, 1H), 7.30 (dd, 1H), 7.92 (d, 1H), 8.05 (s, 1H), 8.43 (d, 1H).

Step D: Preparation of 3-bromo-1-(3-chloro-2-pyridinyl)-1H-pyrazole-5-carboxylic acid To a solution of 2-(3-bromo-1H-pyrazol-1-yl)-3-chloropyridine (i.e. the pyrazole product of Step C) (30.4 g, 118 mmol) in dry tetrahydrofuran (250 mL) at −76° C. was added dropwise a solution of lithium diisopropylamide (118 mmol) in tetrahydrofuran at such a rate as to maintain the temperature below −71° C. The reaction mixture was stirred for 15 minutes at −76° C., and carbon dioxide was then bubbled through for 10 minutes, causing warming to −57° C. The reaction mixture was warmed to −20° C. and quenched with water. The reaction mixture was concentrated and then taken up in water (1 L) and ether (500 mL), and then aqueous sodium hydroxide solution (1 N, 20 mL) was added. The aqueous extracts were washed with ether and acidified with hydrochloric acid. The precipitated solids were filtered, washed with water and dried to afford 27.7 g of the title product as a tan solid. Product from another run following similar procedure melted at 200-201° C.

$^1$H NMR (DMSO-d$_6$): δ 7.25 (s, 1H), 7.68 (dd, 1H), 8.24 (d, 1H), 8.56 (d, 1H).

Step E: Preparation of 2-[3-bromo-1-(3-chloro-2-pyridinyl)-1H-pyrazol-5-yl]-6-iodo-8-methyl-4H-3,1-benzoxazin-4-one To a solution of methanesulfonyl chloride (0.54 ml, 6.94 mmol) in acetonitrile (15 mL) was added dropwise a mixture of 3-bromo-1-(3-chloro-2-pyridinyl)-1H-pyrazole-5-carboxylic acid (i.e. the carboxylic acid product of Step D) (2.0 g, 6.6 mmol) and triethylamine (0.92 ml, 6.6 mmol) in acetonitrile (5 mL) at 0° C. The reaction mixture was then stirred for 15 minutes at 0° C. Then, 2-amino-3-methyl-5-iodobenzoic acid (i.e. the product from Example 1, Step A) (1.8 g, 6.6 mmol) was added, and stirring was continued for an additional 5 minutes. A solution of triethylamine (1.85 mL, 13.2 mmol) in acetonitrile (5 mL) was then added dropwise while keeping the temperature below 5° C. The reaction mixture was stirred. 40 minutes at 0° C., and then methanesulfonyl chloride (0.54 ml, 6.94 mmol) was added. The reaction mixture was then warmed to room temperature and stirred overnight. The reaction mixture was then diluted with water (50 mL) and extracted with ethyl acetate (3×50 mL). The combined ethyl acetate extracts were washed successively with 10% aqueous sodium bicarbonate (1×20 ml) and brine (1×20 mL), dried (MgSO$_4$) and concentrated to afford 2.24 g of the title product as a crude yellow solid.

$^1$H NMR (CDCl$_3$): δ 8.55 (dd, 1H), 8.33 (d, 1H), 7.95 (dd, 1H), 7.85 (s, 1H), 7.45 (m, 1H), 7.25 (s, 1H), 1.77 (s, 3H).

Step F: Preparation of 2-[3-bromo-1-(3-chloro-2-pyridinyl)-1H-pyrazol-5-yl]-6-cyano-8-methyl-4H-3,1-benzoxazin-4-one To a solution of 2-[3-bromo-1-(3-chloro-2-pyridinyl)-1H-pyrazol-5-yl]-6-iodo-8-methyl-4H-3,1-benzoxazin-4-one (i.e. the benzoxazinone product of Step E) (600 mg, 1.1 mmol) in tetrahydrofuran (15 mL) was added copper(I) iodide (126 mg, 0.66 mmol), tetrakis(triphenyphosphine)palladium(0) (382 mg, 0.33 mmol) and copper(I) cyanide (800 mg, 8.8 mmol) sequentially at room temperature. The reaction mixture was then heated at reflux overnight. The reaction turned black in color, at which point thin layer chromatography on silica gel confirmed completion of the reaction. The reaction mixture was diluted with ethyl acetate (20 mL) and filtered through Celite®, followed by washing three times with 10% sodium bicarbonate solution and once with brine. The organic extract was dried (MgSO$_4$) and concentrated under reduced pressure to afford 440 mg of the title compound as a crude yellow solid.

$^1$H NMR (CDCl$_3$): δ 8.55 (m, 1H), 8.3.1 (d, 1H), 7.96 (dd, 1H), 7.73 (s, 1H), 7.51 (m, 1H), 7.31 (s, 1H), 1.86 (s, 3H).

Step G: Preparation of 3-bromo-1-(3-chloro-2-pyridinyl)-N-[4-cyano-2-methyl-6-[(methylamino)carbonyl]phenyl]-1H-pyrazole-5-carboxamide To a solution of 2-[3-bromo-1-(3-chloro-2-pyridinyl)-1H-pyrazol-5-yl]-6-cyano-8-methyl-4H-3,1-benzoxazin-4-one (i.e. the cyanobenzoxazinone product of Step F) (100 mg, 0.22 mmol) in tetrahydrofuran (5 mL) was added dropwise methylamine (2.0 M solution in THF, 0.5 mL, 1.0 mmol) and the reaction mixture was stirred for 5 minutes, at which point thin layer chromatography on silica gel confirmed completion of the reaction. The tetrahydrofuran solvent was evaporated under reduced pressure, and the residual solid was purified by chromatography on silica gel to afford the title compound, a compound of the present invention, as a white solid (41 mg), which decomposed in the melting apparatus above 180° C.

$^1$H NMR (CDCl$_3$): δ 10.55 (s, 1H), 8.45 (dd, 1H), 7.85 (dd, 1H), 7.57 (s, 2H), 7.37 (m, 1H), 7.05 (s, 1H), 6.30 (d, 1H), 2.98 (d, 3H), 2.24 (s, 3H).

Example 6

Preparation of 3-bromo-1-(3-chloro-2-pyridinyl)-N-[4-cyano-2-methyl-6-(aminocarbonyl)phenyl]-1H-pyrazole-5-carboxamide To a solution of 2-[3-bromo-1-(3-chloro-2-pyridinyl)-1H-pyrazol-5-yl]-6-cyano-8-methyl-4H-3,1-benzoxazin-4-one (i.e. the cyanobenzoxazinone product of Example 5, Step F) (100 mg, 0.22 mmol) in tetrahydrofuran (5 mL) was added dropwise ammonium hydroxide (0.5 mL, 12.8 mmol) at room temperature. The reaction mixture was then stirred for five minutes, at which point thin layer chromatography on silica gel confirmed completion of the reaction. The tetrahydrofuran solvent was evaporated under reduced pressure, and the residual solid was purified by chromatography on silica gel to afford the title compound, a compound of the present invention, as a white solid (36 mg), with a melting point above 255° C.

$^1$H NMR (CDCl$_3$): δ10.52 (s, 1H), 8.45 (dd, 1H), 7.85 (dd, 1H), 7.65 (s, 1H), 7.60 (s, 1H), 7.40 (m, 1H), 7.05 (s, 1H), 6.20 (bs, 1H), 5.75 (bs, 1H), 2.25 (s, 3H).

Example 7

Preparation of 3-chloro-1-(3-chloro-2-pyridinyl)-N-[2-chloro-4-cyano-6-[(methylamino)carbonyl]phenyl]-1H-pyrazole-5-carboxamide Step A: Preparation of 2-amino-3-chloro-5-iodobenzoic acid To a solution of 2-amino-3-chlorobenzoic acid (Aldrich, 5 g, 29.1 mmol) in N,N-dimethylformamide (30 mL) was added N-iodosuccinimide (5.8 g, 26 mmol) and the reaction mixture was heated at 60° C. overnight. The heat was removed and the reaction mixture was then slowly poured into ice-water (100 mL) to precipitate a light brown solid. The solid was filtered and washed four times with water and then placed in a vacuum oven at 70° C. to dry overnight. The desired intermediate was isolated as a light brown solid (7.2 g).

$^1$H NMR (DMSO-d): δ 7.96 (d, 1H), 7.76 (t, 1H).

Step B: Preparation of 8-chloro-2-[3-chloro-1-(3-chloro-2-pyridinyl)-1H-pyrazol-5-yl]-6-iodo-4H-3,1-benzoxazin-4-one To a solution of methanesulfonyl chloride (0.31 mL, 4.07 mmol) in acetonitrile (10 mL) was added dropwise a mixture of 3-chloro-1-(3-chloro-2-pyridinyl)-1H-pyrazole-5-carboxylic acid (i.e. the carboxylic acid product of Example 3, Step D) (1.0 g, 3.87 mmol) and triethylamine (0.54 mL, 3.87 mmol) in acetonitrile (5 mL) at 0° C. The reaction mixture was then stirred for 15 minutes at 0° C. Then, 2-amino-3-chloro-5-iodobenzoic acid (i.e. the product from Step A) (1.15 g, 3.87 mmol) was added, and stirring was continued for an additional 5 minutes. A solution of triethylamine (1.08 mL, 7.74 mmol) in acetonitrile (5 mL) was then added dropwise while keeping the temperature below 5° C. The reaction mixture was stirred 40 minutes at 0° C., and then methanesulfonyl chloride (0.31 mL, 4.07 mmol) was added. The reaction mixture was then warmed to room temperature and stirred overnight. The reaction mixture was then diluted with water (50 mL) and extracted with ethyl acetate (3×50 mL). The combined ethyl acetate extracts were washed successively with 10% aqueous sodium bicarbonate (1×20 mL) and brine (1×20 mL), dried (MgSO$_4$) and concentrated under reduced pressure. The residual solid was purified by chromatography on silica gel to afford 575 mg of the title compound as a crude yellow solid.

$^1$H NMR (CDCl$_3$): δ 8.55 (q, 1H), 8.39 (d, 1H), 8.04 (d, 1H), 7.94 (dd, 1H), 7.45 (m, 1H), 7.19 (s, 1H).

Step C: Preparation of 8-chloro-2-[3-chloro-1-(3-chloro-2-pyridinyl)-1H-pyrazol-5-yl]-6-cyano-4H-3,1-benzoxazin-4-one To a solution of 8-chloro-2-[3-chloro-1-(3-chloro-2-pyridinyl)-1H-pyrazol-5-yl]-6-iodo-4H-3,1-benzoxazin-4-one (i.e. the benzoxazinone product of Step B) (575 mg, 1.1 mmol) in tetrahydrofuran (15 mL) was added copper(I) iodide (840 mg, 0.44 mmol), tetrakis(triphenyphosphine)palladium(0) (255 mg, 0.22 mmol) and copper(I) cyanide (500 mg, 5.5 mmol) sequentially at room temperature. The reaction mixture was then heated at reflux overnight. The reaction turned black in color, at which point thin layer chromatography on silica gel confirmed completion of the reaction. The reaction was diluted with ethyl acetate (20 mL) and filtered through Celite®, followed by washing three times with 10% aqueous sodium bicarbonate solution and once with brine. The organic extract was dried (MgSO₄) and concentrated under reduced pressure to afford 375 mg of the title compound as a crude yellow solid.

$^1$H NMR (CDCl₃): δ 8.55 (q, 1H), 8.36 (d, 1H), 7.95 (m, 2H), 7.5 (m, 1H).

Step D: Preparation of 3-chloro-1-(3-chloro-2-pyridinyl)-N-[2-chloro-4-cyano-6-[(methylamino)carbonyl]phenyl]-1H-pyrazole-5-carboxamide To a solution of 8-chloro-2-[3-chloro-1-(3-chloro-2-pyridinyl)-1H-pyrazol-5-yl]-6-cyano-4H-3,1-benzoxazin-4-one (i.e. the cyanobenzoxazinone product of Step C) (187 mg, 0.446 mmol) in tetrahydrofuran (5 mL) was added dropwise methylamine (2.0 M solution in THF, 0.5 mL, 1.0 mmol) and the reaction mixture was stirred for 5 minutes, at which point thin layer chromatography on silica gel confirmed completion of the reaction. The tetrahydrofuran solvent was evaporated under reduced pressure, and the residual solid was purified by chromatography on silica gel to afford 49 mg of the title compound, a compound of the present invention, as a white solid that melted at 197-200° C.

$^1$H NMR (CDCl₃): δ 10.05 (bs, 1H), 8.45 (q, 1H), 7.85 (dd, 1H), 7.70 (d, 1H), 7.59 (d, 1H), 7.38 (m, 1H), 7.02 (s, 1H), 6.35 (d, 1H), 2.94 (d, 3H).

By the procedures described herein together with methods known in the art, the following compounds of Table 1 can be prepared. The following abbreviations are used in the Tables which follow: t means tertiary, s means secondary, n means natural, i means iso, Me means methyl, Et means ethyl, Pr means propyl, i-Pr means isopropyl, Bu means butyl and CN is cyano.

TABLE 1

| R¹ | R² | R³ | R⁴ | R⁵ |
|----|----|----|----|----|
| Me | Cl | F | H | H |
| Me | Cl | F | Me | H |
| Me | Cl | F | Et | H |
| Me | Cl | F | i-Pr | H |
| Me | Cl | F | t-Bu | H |
| Me | Cl | F | CH₂CN | H |
| Me | Cl | F | CH(Me)CH₂SMe | H |
| Me | Cl | F | C(Me)₂CH₂SMe | H |
| Me | Cl | F | Me | Me |
| Me | Cl | Cl | H | H |
| Me | Cl | Cl | Me | H |
| Me | Cl | Cl | Et | H |
| Me | Cl | Cl | i-Pr | H |
| Me | Cl | Cl | t-Bu | H |
| Me | Cl | Cl | CH₂CN | H |
| Me | Cl | Cl | CH(Me)CH₂SMe | H |
| Me | Cl | Cl | C(Me)₂CH₂SMe | H |
| Me | Cl | Cl | Me | Me |
| Me | Cl | Br | H | H |
| Me | Cl | Br | Me | H |
| Me | Cl | Br | Et | H |
| Me | Cl | Br | i-Pr | H |
| Me | Cl | Br | t-Bu | H |
| Me | Cl | Br | CH₂CN | H |
| Me | Cl | Br | CH(Me)CH₂SMe | H |
| Me | Cl | Br | C(Me)₂CH₂SMe | H |
| Me | Cl | Br | Me | Me |
| Me | Br | F | H | H |
| Me | Br | F | Me | H |
| Me | Br | F | Et | H |
| Me | Br | F | i-Pr | H |
| Me | Br | F | t-Bu | H |
| Me | Br | F | CH₂CN | H |
| Me | Br | F | CH(Me)CH₂SMe | H |
| Me | Br | F | C(Me)₂CH₂SMe | H |
| Me | Br | F | Me | Me |
| Me | Br | Cl | H | H |
| Me | Br | Cl | Me | H |
| Me | Br | Cl | Et | H |
| Me | Br | Cl | i-Pr | H |
| Me | Br | Cl | t-Bu | H |
| Me | Br | Cl | CH₂CN | H |
| Me | Br | Cl | CH(Me)CH₂SMe | H |
| Me | Br | Cl | C(Me)₂CH₂SMe | H |
| Me | Br | Cl | Me | Me |
| Me | Br | Br | H | H |
| Me | Br | Br | Me | H |
| Me | Br | Br | Et | H |
| Me | Br | Br | i-Pr | H |
| Me | Br | Br | t-Bu | H |
| Me | Br | Br | CH₂CN | H |
| Me | Br | Br | CH(Me)CH₂SMe | H |
| Me | Br | Br | C(Me)₂CH₂SMe | H |
| Me | Br | Br | Me | Me |
| Me | CF₃ | F | H | H |
| Me | CF₃ | F | Me | H |
| Me | CF₃ | F | Et | H |
| Me | CF₃ | F | i-Pr | H |
| Me | CF₃ | F | t-Bu | H |
| Me | CF₃ | F | CH₂CN | H |
| Me | CF₃ | F | CH(Me)CH₂SMe | H |
| Me | CF₃ | F | C(Me)₂CH₂SMe | H |
| Me | CF₃ | F | Me | Me |
| Me | CF₃ | Cl | H | H |
| Me | CF₃ | Cl | Me | H |
| Me | CF₃ | Cl | Et | H |
| Me | CF₃ | Cl | i-Pr | H |
| Me | CF₃ | Cl | t-Bu | H |
| Me | CF₃ | Cl | CH₂CN | H |
| Me | CF₃ | Cl | CH(Me)CH₂SMe | H |
| Me | CF₃ | Cl | C(Me)₂CH₂SMe | H |
| Me | CF₃ | Cl | Me | Me |
| Me | CF₃ | Br | H | H |

TABLE 1-continued

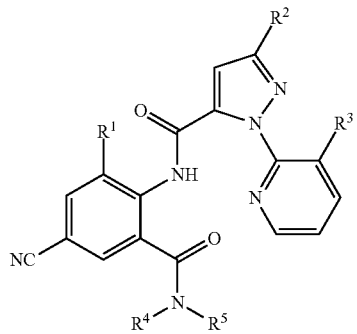

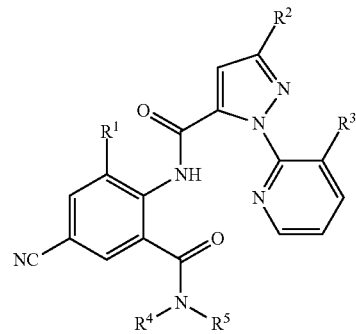

| R¹ | R² | R³ | R⁴ | R⁵ |
|---|---|---|---|---|
| Me | CF₃ | Br | Me | H |
| Me | CF₃ | Br | Et | H |
| Me | CF₃ | Br | i-Pr | H |
| Me | CF₃ | Br | t-Bu | H |
| Me | CF₃ | Br | CH₂CN | H |
| Me | CF₃ | Br | CH(Me)CH₂SMe | H |
| Me | CF₃ | Br | C(Me)₂CH₂SMe | H |
| Me | CF₃ | Br | Me | Me |
| Me | OCF₂H | F | H | H |
| Me | OCF₂H | F | Me | H |
| Me | OCF₂H | F | Et | H |
| Me | OCF₂H | F | i-Pr | H |
| Me | OCF₂H | F | t-Bu | H |
| Me | OCF₂H | F | CH₂CN | H |
| Me | OCF₂H | F | CH(Me)CH₂SMe | H |
| Me | OCF₂H | F | C(Me)₂CH₂SMe | H |
| Me | OCF₂H | F | Me | Me |
| Me | OCF₂H | Cl | H | H |
| Me | OCF₂H | Cl | Me | H |
| Me | OCF₂H | Cl | Et | H |
| Me | OCF₂H | Cl | i-Pr | H |
| Me | OCF₂H | Cl | t-Bu | H |
| Me | OCF₂H | Cl | CH₂CN | H |
| Me | OCF₂H | Cl | CH(Me)CH₂SMe | H |
| Me | OCF₂H | Cl | C(Me)₂CH₂SMe | H |
| Me | OCF₂H | Cl | Me | Me |
| Me | OCF₂H | Br | H | H |
| Me | OCF₂H | Br | Me | H |
| Me | OCF₂H | Br | Et | H |
| Me | OCF₂H | Br | i-Pr | H |
| Me | OCF₂H | Br | t-Bu | H |
| Me | OCF₂H | Br | CH₂CN | H |
| Me | OCF₂H | Br | CH(Me)CH₂SMe | H |
| Me | OCF₂H | Br | C(Me)₂CH₂SMe | H |
| Me | OCF₂H | Br | Me | Me |
| Me | OCH₂CF₃ | F | H | H |
| Me | OCH₂CF₃ | F | Me | H |
| Me | OCH₂CF₃ | F | Et | H |
| Me | OCH₂CF₃ | F | i-Pr | H |
| Me | OCH₂CF₃ | F | t-Bu | H |
| Me | OCH₂CF₃ | F | CH₂CN | H |
| Me | OCH₂CF₃ | F | CH(Me)CH₂SMe | H |
| Me | OCH₂CF₃ | F | C(Me)₂CH₂SMe | H |
| Me | OCH₂CF₃ | F | Me | Me |
| Me | OCH₂CF₃ | Cl | H | H |
| Me | OCH₂CF₃ | Cl | Me | H |
| Me | OCH₂CF₃ | Cl | Et | H |
| Me | OCH₂CF₃ | Cl | i-Pr | H |
| Me | OCH₂CF₃ | Cl | t-Bu | H |
| Me | OCH₂CF₃ | Cl | CH₂CN | H |
| Me | OCH₂CF₃ | Cl | CH(Me)CH₂SMe | H |
| Me | OCH₂CF₃ | Cl | C(Me)₂CH₂SMe | H |
| Me | OCH₂CF₃ | Cl | Me | Me |
| Me | OCH₂CF₃ | Br | H | H |
| Me | OCH₂CF₃ | Br | Me | H |
| Me | OCH₂CF₃ | Br | Et | H |
| Me | OCH₂CF₃ | Br | i-Pr | H |
| Me | OCH₂CF₃ | Br | t-Bu | H |
| Me | OCH₂CF₃ | Br | CH₂CN | H |
| Me | OCH₂CF₃ | Br | CH(Me)CH₂SMe | H |
| Me | OCH₂CF₃ | Br | C(Me)₂CH₂SMe | H |
| Me | OCH₂CF₃ | Br | Me | Me |
| Me | OCF₃ | F | H | H |
| Me | OCF₃ | F | Me | H |
| Me | OCF₃ | F | Et | H |
| Me | OCF₃ | F | i-Pr | H |
| Me | OCF₃ | F | t-Bu | H |
| Me | OCF₃ | F | CH₂CN | H |
| Me | OCF₃ | F | CH(Me)CH₂SMe | H |
| Me | OCF₃ | F | C(Me)₂CH₂SMe | H |
| Me | OCF₃ | F | Me | Me |
| Me | OCF₃ | Cl | H | H |
| Me | OCF₃ | Cl | Me | H |
| Me | OCF₃ | Cl | Et | H |
| Me | OCF₃ | Cl | i-Pr | H |
| Me | OCF₃ | Cl | t-Bu | H |
| Me | OCF₃ | Cl | CH₂CN | H |
| Me | OCF₃ | Cl | CH(Me)CH₂SMe | H |
| Me | OCF₃ | Cl | C(Me)₂CH₂SMe | H |
| Me | OCF₃ | Cl | Me | Me |
| Me | OCF₃ | Br | H | H |
| Me | OCF₃ | Br | Me | H |
| Me | OCF₃ | Br | Et | H |
| Me | OCF₃ | Br | i-Pr | H |
| Me | OCF₃ | Br | t-Bu | H |
| Me | OCF₃ | Br | CH₂CN | H |
| Me | OCF₃ | Br | CH(Me)CH₂SMe | H |
| Me | OCF₃ | Br | C(Me)₂CH₂SMe | H |
| Me | OCF₃ | Br | Me | Me |
| Cl | Cl | F | H | H |
| Cl | Cl | F | Me | H |
| Cl | Cl | F | Et | H |
| Cl | Cl | F | i-Pr | H |
| Cl | Cl | F | t-Bu | H |
| Cl | Cl | F | CH₂CN | H |
| Cl | Cl | F | CH(Me)CH₂SMe | H |
| Cl | Cl | F | C(Me)₂CH₂SMe | H |
| Cl | Cl | F | Me | Me |
| Cl | Cl | Cl | H | H |
| Cl | Cl | Cl | Me | H |
| Cl | Cl | Cl | Et | H |
| Cl | Cl | Cl | i-Pr | H |
| Cl | Cl | Cl | t-Bu | H |
| Cl | Cl | Cl | CH₂CN | H |
| Cl | Cl | Cl | CH(Me)CH₂SMe | H |
| Cl | Cl | Cl | C(Me)₂CH₂SMe | H |
| Cl | Cl | Cl | Me | Me |
| Cl | Cl | Br | H | H |
| Cl | Cl | Br | Me | H |
| Cl | Cl | Br | Et | H |
| Cl | Cl | Br | i-Pr | H |
| Cl | Cl | Br | t-Bu | H |
| Cl | Cl | Br | CH₂CN | H |
| Cl | Cl | Br | CH(Me)CH₂SMe | H |
| Cl | Cl | Br | C(Me)₂CH₂SMe | H |
| Cl | Cl | Br | Me | Me |
| Cl | Br | F | H | H |
| Cl | Br | F | Me | H |
| Cl | Br | F | Et | H |
| Cl | Br | F | i-Pr | H |

TABLE 1-continued

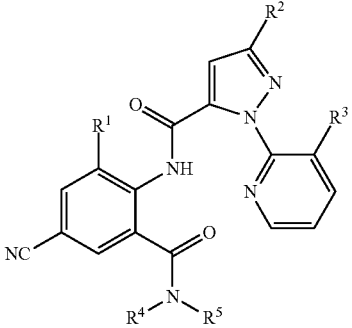

| R¹ | R² | R³ | R⁴ | R⁵ |
|---|---|---|---|---|
| Cl | Br | F | t-Bu | H |
| Cl | Br | F | $CH_2CN$ | H |
| Cl | Br | F | $CH(Me)CH_2SMe$ | H |
| Cl | Br | F | $C(Me)_2CH_2SMe$ | H |
| Cl | Br | F | Me | Me |
| Cl | Br | Cl | H | H |
| Cl | Br | Cl | Me | H |
| Cl | Br | Cl | Et | H |
| Cl | Br | Cl | i-Pr | H |
| Cl | Br | Cl | t-Bu | H |
| Cl | Br | Cl | $CH_2CN$ | H |
| Cl | Br | Cl | $CH(Me)CH_2SMe$ | H |
| Cl | Br | Cl | $C(Me)_2CH_2SMe$ | H |
| Cl | Br | Cl | Me | Me |
| Cl | Br | Br | H | H |
| Cl | Br | Br | Me | H |
| Cl | Br | Br | Et | H |
| Cl | Br | Br | i-Pr | H |
| Cl | Br | Br | t-Bu | H |
| Cl | Br | Br | $CH_2CN$ | H |
| Cl | Br | Br | $CH(Me)CH_2SMe$ | H |
| Cl | Br | Br | $C(Me)_2CH_2SMe$ | H |
| Cl | Br | Br | Me | Me |
| Cl | $CF_3$ | F | H | H |
| Cl | $CF_3$ | F | Me | H |
| Cl | $CF_3$ | F | Et | H |
| Cl | $CF_3$ | F | i-Pr | H |
| Cl | $CF_3$ | F | t-Bu | H |
| Cl | $CF_3$ | F | $CH_2CN$ | H |
| Cl | $CF_3$ | F | $CH(Me)CH_2SMe$ | H |
| Cl | $CF_3$ | F | $C(Me)_2CH_2SMe$ | H |
| Cl | $CF_3$ | F | Me | Me |
| Cl | $CF_3$ | Cl | H | H |
| Cl | $CF_3$ | Cl | Me | H |
| Cl | $CF_3$ | Cl | Et | H |
| Cl | $CF_3$ | Cl | i-Pr | H |
| Cl | $CF_3$ | Cl | t-Bu | H |
| Cl | $CF_3$ | Cl | $CH_2CN$ | H |
| Cl | $CF_3$ | Cl | $CH(Me)CH_2SMe$ | H |
| Cl | $CF_3$ | Cl | $C(Me)_2CH_2SMe$ | H |
| Cl | $CF_3$ | Cl | Me | Me |
| Cl | $CF_3$ | Br | H | H |
| Cl | $CF_3$ | Br | Me | H |
| Cl | $CF_3$ | Br | Et | H |
| Cl | $CF_3$ | Br | i-Pr | H |
| Cl | $CF_3$ | Br | t-Bu | H |
| Cl | $CF_3$ | Br | $CH_2CN$ | H |
| Cl | $CF_3$ | Br | $CH(Me)CH_2SMe$ | H |
| Cl | $CF_3$ | Br | $C(Me)_2CH_2SMe$ | H |
| Cl | $CF_3$ | Br | Me | Me |
| Cl | $OCF_2H$ | F | H | H |
| Cl | $OCF_2H$ | F | Me | H |
| Cl | $OCF_2H$ | F | Et | H |
| Cl | $OCF_2H$ | F | i-Pr | H |
| Cl | $OCF_2H$ | F | t-Bu | H |
| Cl | $OCF_2H$ | F | $CH_2CN$ | H |
| Cl | $OCF_2H$ | F | $CH(Me)CH_2SMe$ | H |
| Cl | $OCF_2H$ | F | $C(Me)_2CH_2SMe$ | H |
| Cl | $OCF_2H$ | F | Me | Me |
| Cl | $OCF_2H$ | Cl | H | H |

TABLE 1-continued

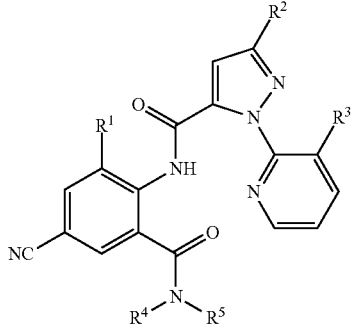

| R¹ | R² | R³ | R⁴ | R⁵ |
|---|---|---|---|---|
| Cl | $OCF_2H$ | Cl | Me | H |
| Cl | $OCF_2H$ | Cl | Et | H |
| Cl | $OCF_2H$ | Cl | i-Pr | H |
| Cl | $OCF_2H$ | Cl | t-Bu | H |
| Cl | $OCF_2H$ | Cl | $CH_2CN$ | H |
| Cl | $OCF_2H$ | Cl | $CH(Me)CH_2SMe$ | H |
| Cl | $OCF_2H$ | Cl | $C(Me)_2CH_2SMe$ | H |
| Cl | $OCF_2H$ | Cl | Me | Me |
| Cl | $OCF_2H$ | Br | H | H |
| Cl | $OCF_2H$ | Br | Me | H |
| Cl | $OCF_2H$ | Br | Et | H |
| Cl | $OCF_2H$ | Br | i-Pr | H |
| Cl | $OCF_2H$ | Br | t-Bu | H |
| Cl | $OCF_2H$ | Br | $CH_2CN$ | H |
| Cl | $OCF_2H$ | Br | $CH(Me)CH_2SMe$ | H |
| Cl | $OCF_2H$ | Br | $C(Me)_2CH_2SMe$ | H |
| Cl | $OCF_2H$ | Br | Me | Me |
| Cl | $OCH_2CF_3$ | F | H | H |
| Cl | $OCH_2CF_3$ | F | Me | H |
| Cl | $OCH_2CF_3$ | F | Et | H |
| Cl | $OCH_2CF_3$ | F | i-Pr | H |
| Cl | $OCH_2CF_3$ | F | t-Bu | H |
| Cl | $OCH_2CF_3$ | F | $CH_2CN$ | H |
| Cl | $OCH_2CF_3$ | F | $CH(Me)CH_2SMe$ | H |
| Cl | $OCH_2CF_3$ | F | $C(Me)CH_2SMe$ | H |
| Cl | $OCH_2CF_3$ | F | Me | Me |
| Cl | $OCH_2CF_3$ | Cl | H | H |
| Cl | $OCH_2CF_3$ | Cl | Me | H |
| Cl | $OCH_2CF_3$ | Cl | Et | H |
| Cl | $OCH_2CF_3$ | Cl | i-Pr | H |
| Cl | $OCH_2CF_3$ | Cl | t-Bu | H |
| Cl | $OCH_2CF_3$ | Cl | $CH_2CN$ | H |
| Cl | $OCH_2CF_3$ | Cl | $CH(Me)CH_2SMe$ | H |
| Cl | $OCH_2CF_3$ | Cl | $C(Me)_2CH_2SMe$ | H |
| Cl | $OCH_2CF_3$ | Cl | Me | Me |
| Cl | $OCH_2CF_3$ | Br | H | H |
| Cl | $OCH_2CF_3$ | Br | Me | H |
| Cl | $OCH_2CF_3$ | Br | Et | H |
| Cl | $OCH_2CF_3$ | Br | i-Pr | H |
| Cl | $OCH_2CF_3$ | Br | t-Bu | H |
| Cl | $OCH_2CF_3$ | Br | $CH_2CN$ | H |
| Cl | $OCH_2CF_3$ | Br | $CH(Me)CH_2SMe$ | H |
| Cl | $OCH_2CF_3$ | Br | $C(Me)_2CH_2SMe$ | H |
| Cl | $OCH_2CF_3$ | Br | Me | Me |
| Cl | $OCF_3$ | F | H | H |
| Cl | $OCF_3$ | F | Me | H |
| Cl | $OCF_3$ | F | Et | H |
| Cl | $OCF_3$ | F | i-Pr | H |
| Cl | $OCF_3$ | F | t-Bu | H |
| Cl | $OCF_3$ | F | $CH_2CN$ | H |
| Cl | $OCF_3$ | F | $CH(Me)CH_2SMe$ | H |
| Cl | $OCF_3$ | F | $C(Me)_2CH_2SMe$ | H |
| Cl | $OCF_3$ | F | Me | Me |
| Cl | $OCF_3$ | Cl | H | H |
| Cl | $OCF_3$ | Cl | Me | H |
| Cl | $OCF_3$ | Cl | Et | H |
| Cl | $OCF_3$ | Cl | i-Pr | H |
| Cl | $OCF_3$ | Cl | t-Bu | H |
| Cl | $OCF_3$ | Cl | $CH_2CN$ | H |
| Cl | $OCF_3$ | Cl | $CH(Me)CH_2SMe$ | H |

TABLE 1-continued

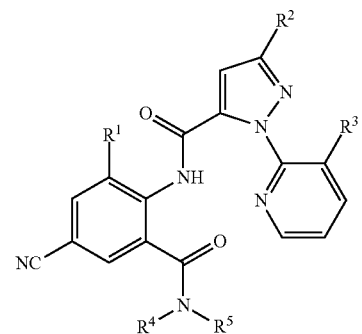

| R¹ | R² | R³ | R⁴ | R⁵ |
|----|----|----|----|----|
| Cl | OCF$_3$ | Cl | C(Me)$_2$CH$_2$SMe | H |
| Cl | OCF$_3$ | Cl | Me | Me |
| Cl | OCF$_3$ | Br | H | H |
| Cl | OCF$_3$ | Br | Me | H |
| Cl | OCF$_3$ | Br | Et | H |
| Cl | OCF$_3$ | Br | i-Pr | H |
| Cl | OCF$_3$ | Br | t-Bu | H |
| Cl | OCF$_3$ | Br | CH$_2$CN | H |
| Cl | OCF$_3$ | Br | CH(Me)CH$_2$SMe | H |
| Cl | OCF$_3$ | Br | C(Me)$_2$CH$_2$SMe | H |
| Cl | OCF$_3$ | Br | Me | Me |

TABLE 2

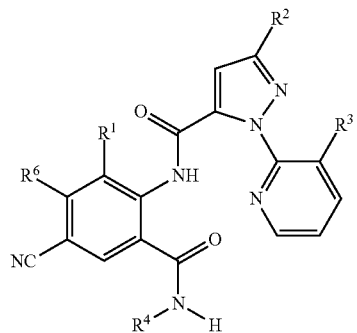

| R¹ | R² | R³ | R⁴ | R⁶ | R¹ | R² | R³ | R⁴ | R⁶ |
|----|----|----|----|----|----|----|----|----|----|
| Me | CF$_3$ | Cl | Me | F | Me | CF$_3$ | Cl | Me | Cl |
| Cl | CF$_3$ | Cl | Me | F | Cl | CF$_3$ | Cl | Me | Cl |
| Br | CF$_3$ | Cl | Me | F | Br | CF$_3$ | Cl | Me | Cl |
| Me | Cl | Cl | Me | F | Me | Cl | Cl | Me | Cl |
| Cl | Cl | Cl | Me | F | Cl | Cl | Cl | Me | Cl |
| Br | Cl | Cl | Me | F | Br | Cl | Cl | Me | Cl |
| Me | Br | Cl | Me | F | Me | Br | Cl | Me | Cl |
| Cl | Br | Cl | Me | F | Cl | Br | Cl | Me | Cl |
| Br | Br | Cl | Me | F | Br | Br | Cl | Me | Cl |
| Me | CF$_3$ | Cl | i-Pr | F | Me | CF$_3$ | Cl | i-Pr | Cl |
| Cl | CF$_3$ | Cl | i-Pr | F | Cl | CF$_3$ | Cl | i-Pr | Cl |
| Br | CF$_3$ | Cl | i-Pr | F | Br | CF$_3$ | Cl | i-Pr | Cl |
| Me | Cl | Cl | i-Pr | F | Me | Cl | Cl | i-Pr | Cl |
| Cl | Cl | Cl | i-Pr | F | Cl | Cl | Cl | i-Pr | Cl |
| Br | Cl | Cl | i-Pr | F | Br | Cl | Cl | i-Pr | Cl |
| Me | Br | Cl | i-Pr | F | Me | Br | Cl | i-Pr | Cl |
| Cl | Br | Cl | i-Pr | F | Cl | Br | Cl | i-Pr | Cl |
| Br | Br | Cl | i-Pr | F | Br | Br | Cl | i-Pr | Cl |

TABLE 3

| R¹ | R² | R³ | R⁴ | R⁷ | R¹ | R² | R³ | R⁴ | R⁷ |
|----|----|----|----|----|----|----|----|----|----|
| Me | CF$_3$ | F | Me | F | Me | CF$_3$ | Cl | Me | Cl |
| Cl | CF$_3$ | F | Me | F | Cl | CF$_3$ | Cl | Me | Cl |
| Br | CF$_3$ | F | Me | F | Br | CF$_3$ | Cl | Me | Cl |
| Me | Cl | F | Me | F | Me | Cl | Cl | Me | Cl |
| Cl | Cl | F | Me | F | Cl | Cl | Cl | Me | Cl |
| Br | Cl | F | Me | F | Br | Cl | Cl | Me | Cl |
| Me | Br | F | Me | F | Me | Br | Cl | Me | Cl |
| Cl | Br | F | Me | F | Cl | Br | Cl | Me | Cl |
| Br | Br | F | Me | F | Br | Br | Cl | Me | Cl |
| Me | CF$_3$ | F | i-Pr | F | Me | CF$_3$ | Cl | i-Pr | Cl |
| Cl | CF$_3$ | F | i-Pr | F | Cl | CF$_3$ | Cl | i-Pr | Cl |
| Br | CF$_3$ | F | i-Pr | F | Br | CF$_3$ | Cl | i-Pr | Cl |
| Me | Cl | F | i-Pr | F | Me | Cl | Cl | i-Pr | Cl |
| Cl | Cl | F | i-Pr | F | Cl | Cl | Cl | i-Pr | Cl |
| Br | Cl | F | i-Pr | F | Br | Cl | Cl | i-Pr | Cl |
| Me | Br | F | i-Pr | F | Me | Br | Cl | i-Pr | Cl |
| Cl | Br | F | i-Pr | F | Cl | Br | Cl | i-Pr | Cl |
| Br | Br | F | i-Pr | F | Br | Br | Cl | i-Pr | Cl |

Formulation/Utility

Compounds of this invention will generally be used as a formulation or composition with a carrier suitable for agronomic or nonagronomic use comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further fowled into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 5-90 | 0-94 | 1-15 |
| Suspensions, Emulsions, Solutions (including Emulsifiable Concentrates) | 5-50 | 40-95 | 0-15 |
| Dusts | 1-25 | 70-99 | 0-5 |
| Granules and Pellets | 0.01-99 | 5-99.99 | 0-15 |
| High Strength Compositions | 90-99 | 0-10 | 0-2 |

Typical solid diluents are described in Watkins, et al., *Handbook of Insecticide Dust Diluents and Carriers*, 2nd Ed., Dorland Books, Caldwell, N.J., Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses, All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tong, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133, See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Table A.

Example A

| Wettable Powder | |
| --- | --- |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

| Granule | |
| --- | --- |
| Compound 1 | 10.0% |
| attapulgite granules (low volatile matter, 0.71/0.30 mm; U.S.S. No. 25-50 sieves) | 90.0%. |

Example C

| Extruded Pellet | |
| --- | --- |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

| Emulsifiable Concentrate | |
| --- | --- |
| Compound 1 | 20.0% |
| blend of oil soluble sulfonates and polyoxyethylene ethers | 10.0% |
| isophorone | 70.0%. |

Example E

| Granule | |
|---|---|
| Compound 1 | 0.5% |
| cellulose | 2.5% |
| lactose | 4.0% |
| cornmeal | 93.0%. |

Compounds of this invention are characterized by favorable metabolic and/or soil residual patterns and exhibit activity controlling a spectrum of agronomic and non-agronomic invertebrate pests. Compounds of this invention are also characterized by favorable foliar and or soil-applied systemicity in plants exhibiting translocation to protect foliage and other plant parts not directly contacted with insecticidal compositions comprising the present compounds. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagons nematodes (Nematoda), flukes (Trematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), turf (commercial, golf, residential, recreational, etc.), wood products, public (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms; cutworms, loopers, and heliothines in the family Noctuidae (e.g., fall armyworm (*Spodoptera fugiperda* J. E. Smith), beet armyworm (*Spodoptera exigua* Hübner); black cutworm (*Agrotis ipsilon* Hufuagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukabo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus olyzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition agronomic and nonagronomic pests include: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included as agronomic and non-agronomic pests are adults and larvae of the order Acari (mites) such as spider mites and red mites in the family Tetranychidae (e.g., European red mite (*Panonychus ulini* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus Zewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinzpes* Fabricius, *M. differentia-* lis Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinella frit* Linnaeus), soil maggots, house flies (e.g., *Musca domestica* Linnaeus), lesser house flies (e.g., *Fannie canicularis* Linnaeus, *F. femoralis* Stein), stable flies (e.g., *Stonioxys caloitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman), flower thrips (*Frankliniella* spp.), and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridamyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets, wasps, and sawflies (*Neodiprion* spp.; *Cephus* spp.); insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisima saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse, (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Douche), dog flea (*Ctenocephalides canis* Curtis), hen flea (*Ceratophyllus gallinae* Schrank), sticktight flea (*Echidnopliaga gallinacea* Westwood), human flea (*Pulex irritans* Linnaeus) and other fleas afflicting mammals and birds. Additional invertebrate pests covered includeK spiders in the order Araneae such as the brown recluse spider (*Loxosceles recluse* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other Archips species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Sanders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid); *Eriosoma lanigerum* Hausmann (woolly apple aphid), *Hyalopterus pruni* Geoffloy (mealy plum aphid), *Lipaphis erysimi* Kaltenbach (turnip aphid), *Metopolophium dirrhodum* Walker (cereal aphid), *Macrosipum eziphorbicze* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopaloszphum padi* Linnaeus (bird cherry-oat aphid), *Schizaphis grarninum* Rondani (greenbug), *Sitobion avenae* Fabricius (English grain aphid), *Therioaphis maculate* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastairix* Pergaude (pecan phylloxera); *Bemisia tabaci* Germadius (tobacco whitefly, sweetpotato whitefly), *Bemisia argentifolii* Bellows & Perring (silverleaf whitefly), *Dialeurodes cirri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotehtx cinticeps* Uhler (green leafhopper), *Nephotettix nigropktus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus cirri* Risso (citrus mealybug); *Pseudococcus* spp. (other mealybug complex); *Cacopsylla pyricola* Foerster (pear psylla), *Trioza diospyri* Ashmead (persimmon psylla). These compounds also have activity on members from the order Hemiptera *Acrosternum hilare* Say (green, stink bug), *Anasa tristis* De Geer (squash bug), *Blissus leucopterus* leucopterus Say (chinch bug), *Corythuca gossypii* Fabricius (cotton lace bug), *Cyrtopeitis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeitus fasciatus* Dallas (large milkweed bug), *Pseudatomoscelis seriatus* Router (cotton fleahopper). Other insect orders controlled by compounds of the invention include Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and non-agronomic utility. Thus the present invention also pertains to a composition comprising a biologically effective amount of a compound of Formula 1 and an effective amount of at least one additional biologically active compound or agent and can further comprise at least one of a surfactant, a solid diluent or a liquid diluent. Examples of such biologically active compounds or agents with which compounds of this invention can be formulated are: insecticides such as abamectin, acephate, acetamiprid, acetoprole, amidoflumet (S-1955), avermectin, azadirachtin, azinphos-methyl, bifenthrin, bifenazate, bistrifluoron, buprofezin, carbofuran, chlorfenapyr, chlorofluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, denotefuran, diofenolan, enamectin, endosulfan, esfenvalerate, ethiprole, fenothicarb, fenoxycarb, fenpropathrin, fenvalerate, fipronil, flonicamid, flucythrinate, tan-fluvalinate, flufenerim (UR-50701), flufenoxuron, gamma-chalothrin, halofenozide, hexaflumuron, imidacloprid, indoxacarb, isofenphos, lufenuron, malathion, metaldehyde, methamidophos, methidathion, methomyl, methoprene, methoxychlor, methoxyfenozide, metoflurthrin, monocrotophos, methoxyfenozide, novaluron, noviflumuron (XDE-007), oxamyl, parathion, parathion-methyl, permethrin, phorate, phosalone, phosmet, phosphamidon, pirimicarb, profenofos, profluthrin, protrifenbute, pymetrozine, pyridalyl, pyriproxyfen, rotenone, S1812 (Valent) spinosad, spiromesifen (BSN 2060), sulprofos, tebufenozide, teflubenzuron, tefluthrin, terbufos, tetrachlorvinphos, thiacloprid, thiarnethoxam, thiodicarb, thiosultap-sodium, tolfenpyrad, tralomethrin, trichlorfon and triflnmuron; fungicides such as acibenzolar, S-methyl, azoxystrobin, benalazy-M, benthiavalicarb, benomyl, blasticidin-S, Bordeaux mixture (tribasic copper sulfate), boscalid, bromuconazole, buthiobate, carpropamid, captafol, captan, carbendazim, chloroneb, chlorothalonil, clotrimazole, copper oxychloride, copper salts, cymoxanil, cyazofamid, cyflufenamid, cyproconazole, cyprodinil, diclocymet, diclomezine, dicloran, difenoconazole, dimetliomorph, ditnoxystrobin, diniconazole, diniconazole-M, dodine, edifenphos, epoxiconazole, ethaboxam, famoxadone, fenarimol, fenbuconazole, fenhexamid, fenoxanil, fenpiclonil, fenpropidin, fenpropimorph, fentin acetate, fentin hydroxide, fluazinam, fludioxonil, flumorph, fluoxastrobin, fluquinconazole, flusilazole, flutolanil, flutriafol, folpet, fosetyl-aluminum, furalaxyl, furametapyr, guazatine, hexaconazole, hymexazol, imazalil, imibenxonazole, iminoctadine, ipconazole, iprobenfos, iprodione, iprovalicarb, isoconazole, isoprothiolane, kasugamycin, kresoxim-methyl, mancozeb, maneb, mefenoxam, mepanapyrim, mepronil, metalaxyl, metconazole, metominostrobin/fenominostrobin, metrafenone, miconazole, myclobutanil, neo-asozin (ferric methanearsonate), nuarimol, oryzastrobin, oxadixyl, oxpoconazole, penconazole, pencycuron, picobenzamid, picoxystrobin, probenazole, prochloraz, propamocarb, propiconazole, proquinazid, prothioconazole, pyraclostrobin, pyrimethanil, pyrifenox, pyroquilon, quinoxyfen, silthiofam, simeconazole, sipconazole, spiroxamine, sulfur, tebuconazole, tetraconazole, tiadinil, thiabendazole, thifluzamide, thiophanate-methyl, thiram, tolylfluanid, triadiniefon, triadimenol, triarimol, tricyclazole, trifloxystrobin, triflumizole, triforine, triticonazole, uniconazole, validamycin, vinclozolin and zoxamicle; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki*, *Bacillus thuringiensis* delta endotoxin, baculovirus, and entomopathogenic bacteria, virus and fungi. Compounds of this invention and compositions thereof can be applied to plants genetically transformed to express proteins toxic to invertebrate pests (such as *Bacillus thuringiensis* toxin). The effect of the exogenously applied invertebrate pest control compounds of this invention may be synergistic with the expressed toxin proteins.

A general reference for these agricultural protectants is *The Pesticide Manual*, 12th Edition, C. D. S. Tomlin, Ed., British Crop Protection Council, Farnham, Surrey, U.K., 2000.

Preferred insecticides and acaricides for mixing with compounds of this invention include pyrethroids such as acetamiprid, cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacioprid; neuronal Sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus*

*thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* aizawai or *Bacillus thuringiensis* kurstaki, and a mixture of a compound of this invention with *Bacillus thuringiensis* delta endotoxin.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of invention can also provide a broader spectrum of plant protection and be advantageous for resistance management.

Invertebrate pests are controlled in agronomic and nonagronomic applications by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of invertebrates in agronomic and/or nonagronomic applications, comprising contacting the invertebrates or their environment with a biologically effective amount of one or more of the compounds of the invention, or with a composition comprising at least one such compound or a composition comprising at least one such compound and an effective amount of at least one additional biologically active compound or agent. Examples of suitable compositions comprising a compound of the invention and an effective amount of at least one additional biologically active compound or agent include granular compositions wherein the additional biologically active compound is present on the same granule as the compound of the invention or on granules separate from those of the compound of this invention.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, gels, seed coatings, microencapsulations, systemic uptake, baits, eartags, boluses, foggers, fumigants, aerosols, dusts and many others. The compounds of this invention may also be impregnated into materials for fabricating invertebrate control devices (e.g. insect netting).

A compound of this invention can be incorporated into a bait composition that is consumed by an invertebrate pest or used within devices such as traps, bait stations, and the like. Such a bait composition can be in the form of granules which comprise (a) an active ingredient, namely a compound of Formula 1, an N-oxide, or salt thereof, (b) one or more food materials, (c) optionally an attractant, and (d) optionally one or more humectants. Of note granules or bait compositions which comprise between about 0.001-5% active ingredient; about 40-99% food material and/or attractant; and optionally about 0.05-10% humectants; are effective in controlling soil invertebrate pests at very low application rates, particularly at doses of active ingredient that are lethal by ingestion rather than by direct contact. Of note some food materials will function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents Down to attract a target invertebrate pest. Examples of humectants, i.e. moisture retaining agents, are glycols and other polyols, glycerine and sorbitol. Of note is a bait composition (and a method utilizing such a bait composition) used to control invertebrate pests including individually or in combinations ants, termites, and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The compounds of this invention can be applied in their pure state, but most often application will be of a formulation comprising one or more compounds with suitable carriers, diluents, and surfactants and possibly in combination with a food depending on the contemplated end use A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or ether container, either by means of a pump or by releasing it from a pressurized container, e.g. a pressurized aerosol spray can. Such spray compositions can take various fauns, for example, sprays, mists, foams, fumes or fog. Such spray compositions thus can further comprise propellants, foaming agents, etc. as the case may be. Of note is a spray composition comprising a compound or composition of the present invention and a propellant. Representative propellants include, but are not limited to, methane, ethane, propane, iospropane, butane, isobutane, butene, pentane, iospentane, neopentane, pentene, hydrofluorocarbons, chlorofluoroacarbons, dimethyl ether, and mixtures of the foregoing. Of note is a spray composition (and a method utilizing such a spray composition dispensed from a spray container) used to control an invertebrate pest including individually or in combinations mosquitoes, black flies, stable flies, deer flies, horse flies, wasps, yellow jackets, hornets, ticks, spiders, ants, gnats, and the like.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following TESTS demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Table A, B and C for compound descriptions. The following abbreviations are used in the Index Tables which follow: i is iso, t is tertiary, Me is methyl, Et is ethyl, Pr is propyl, i-Pr is, isopropyl, c-Pr is cyclopropyl, Bu is butyl, and CN is cyano. The abbreviation "Ex." stands for "Example" and is followed by a number indicating in which example, the compound is prepared.

INDEX TABLE A

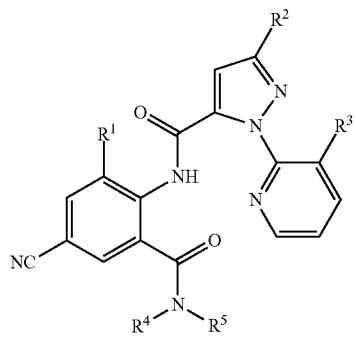

| Compound | $R^1$ | $R^2$ | $R^3$ | $R^4$ | $R^5$ | m.p. (° C.) |
|---|---|---|---|---|---|---|
| 1 (Ex. 1) | Me | CF$_3$ | Cl | H | H | 200-202 |
| 2 (Ex. 2) | Me | CF$_3$ | Cl | Me | H | 214-216 |
| 3 (Ex. 3) | Me | Cl | Cl | Me | H | * |
| 4 (Ex. 4) | Me | Cl | Cl | H | H | >255 |
| 5 (Ex. 5) | Me | Br | Cl | Me | H | * |
| 6 (Ex. 6) | Me | Br | Cl | H | H | >255 |
| 7 (Ex. 7) | Cl | Cl | Cl | Me | H | 197-200 |
| 8 | Me | CF$_3$ | Cl | i-Pr | H | >250 |
| 9 | Cl | Cl | Cl | i-Pr | H | 213-215 |
| 10 | Cl | Br | Cl | i-Pr | H | 222-225 |
| 11 | Cl | Br | Cl | i-Pr | Me | 224-226 |

INDEX TABLE A-continued

| Compound | $R^1$ | $R^2$ | $R^3$ | $R^4$ | $R^5$ | m.p. (° C.) |
|---|---|---|---|---|---|---|
| 12 | Cl | Br | Cl | Me | H | 198-201 |
| 13 | Cl | Cl | Cl | i-Pr | Me | 238-241 |
| 14 | Cl | Br | Cl | H | H | >255 |
| 15 | Cl | F | Cl | i-Pr | H | 162-166 |
| 16 | Cl | F | Cl | Me | H | 205-208 |
| 17 | Cl | Br | F | i-Pr | H | 230-232 |
| 18 | Cl | Br | F | Me | H | * |
| 19 | Cl | Br | F | H | H | >255 |
| 20 | Me | CF$_3$ | Cl | Me | Me | 227-230 |
| 21 | Cl | CF$_3$ | Cl | i-Pr | H | 247-249 |
| 22 | Cl | CF$_3$ | Cl | Me | H | 215-217 |
| 23 | Cl | CF$_3$ | Cl | H | H | >255 |
| 24 | Me | Cl | Cl | i-Pr | H | * |
| 25 | Me | Br | Cl | i-Pr | H | * |
| 26 | Me | Cl | Cl | CH$_2$CN | H | 213-215 |
| 27 | Me | Br | Cl | CH$_2$CN | H | 225-227 |
| 28 | Me | OCH$_2$CF$_3$ | Cl | Me | Me | 132-135 |
| 29 | Me | OCH$_2$CF$_3$ | Cl | Me | H | 162-165 |
| 30 | Me | CF$_3$ | Cl | t-Bu | H | >250 |
| 31 | Me | CF$_3$ | Cl | CH$_2$CN | H | 250-251 |
| 32 | Me | CF$_3$ | Cl | Et | H | 150-151 |
| 33 | Me | Cl | Cl | Et | H | * |
| 34 | Me | Cl | Cl | t-Bu | H | >255 |
| 35 | Me | Br | Cl | Et | H | * |
| 36 | Me | Br | Cl | t-Bu | H | >255 |
| 37 | Me | CF$_3$ | Cl | CH(CH$_3$)CH$_2$SMe | H | 208-209 |
| 39 | Me | Br | Cl | Me | Me | 262-264 |
| 40 | Me | OCH$_2$CF$_3$ | Cl | i-Pr | H | 164-167 |
| 41 | Me | OCH$_2$CF$_3$ | Cl | t-Bu | H | * |
| 42 | Me | OCH$_2$CF$_3$ | Cl | Me | Me | 212-214 |
| 43 | Me | OCH$_2$CF$_3$ | Cl | Et | H | 168-171 |
| 44 | Me | OCH$_2$CF$_3$ | Cl | CH$_2$CN | H | 207-211 |
| 45 | Me | Cl | Cl | Me | Me | 261-263 |
| 46 | Me | CF$_3$ | F | Me | H | 211-212 |
| 47 | Me | CF$_3$ | F | H | H | 138-139 |
| 48 | Me | CF$_3$ | F | Et | H | 219-220 |
| 49 | Me | Br | F | Me | H | 152-153 |
| 50 | Me | Br | F | H | H | 162-164 |
| 51 | Me | Br | F | Et | H | 201-202 |
| 52 | Me | CF$_3$ | F | i-Pr | H | 229-230 |
| 53 | Me | Br | F | i-Pr | H | 159-160 |
| 54 | Me | CF$_3$ | F | CH(CH$_3$)CH$_2$SMe | H | 209-210 |
| 55 | F | Br | Cl | Me | H | 209-210 |
| 63 | Me | Br | Cl | CH(CH$_3$)CH$_2$SMe | H | 180-181 |
| 64 | Me | Cl | Cl | CH(CH$_3$)CH$_2$SMe | H | 193-194 |
| 65 | Me | Br | Cl | C(CH$_3$)$_2$CH$_2$SMe | H | 161-162 |
| 66 | Me | CF$_3$ | Cl | C(CH$_3$)$_2$CH$_2$SMe | H | 250-250 |
| 67 | Me | Cl | Cl | C(CH$_3$)$_2$CH$_2$SMe | H | 234-235 |
| 68 | Me | CF$_3$ | Cl | c-Pr | H | 159-160 |
| 69 | Me | CF$_3$ | Cl | (CH$_2$)$_2$OMe | H | 206-207 |
| 70 | Me | Cl | Cl | c-Pr | H | 156-157 |
| 71 | Me | Cl | Cl | (CH$_2$)$_2$OMe | H | 118-119 |
| 72 | Me | Br | Cl | (CH$_2$)$_2$OMe | H | 216-217 |
| 73 | Me | Br | Cl | c-Pr | H | 159-160 |
| 74 | Me | CF$_3$ | Cl | Me | H | 235-236 |
| 75 | Me | CF$_3$ | Cl | CH$_2$CH(CH$_3$)$_2$ | H | 257-258 |
| 76 | Me | Br | Cl | CH$_2$(c-Pr) | H | 223-224 |
| 77 | Me | Br | Cl | CH$_2$CH(CH$_3$)$_2$ | H | 245-246 |
| 78 | Me | Br | Cl | CH(CH$_3$)CH$_2$S(O)Me | H | 157-158 |
| 79 | Me | Br | Cl | CH(CH$_3$)CH$_2$S(O)$_2$Me | H | 169-170 |

INDEX TABLE A-continued

| Compound | R¹ | R² | R³ | R⁴ | R⁵ | m.p. (° C.) |
|---|---|---|---|---|---|---|
| 80 | Me | Cl | Cl | CH(CH₃)(CH₂)₂SMe | H | 190-191 |
| 81 | Me | Br | Cl | CH(CH₃)(CH₂)₂SMe | H | 188-190 |
| 82 | Me | CF₃ | Cl | CH(CH₃)(CH₂)₂SMe | H | 134-135 |
| 83 | Me | Cl | Cl | CH(CH₃)(CH₂)₂S(O)₂Me | H | 186-187 |
| 84 | Me | Br | Cl | CH(CH₃)(CH₂)₂S(O)₂Me | H | 182-183 |
| 85 | Br | Br | Cl | Me | H | 214-215 |
| 86 | Br | Br | Cl | i-Pr | H | 166-167 |
| 87 | Br | Br | Cl | CH₂CN | H | 226-227 |
| 88 | Me | Cl | F | Me | H | 149-150 |
| 89 | Me | Cl | F | H | H | 146-147 |
| 90 | Me | Cl | Br | H | H | 189-190 |
| 91 | Me | Cl | Br | Me | H | 149-150 |
| 92 | Me | Cl | Br | i-Pr | H | 119-120 |
| 93 | Me | Cl | Br | Me | Me | 247-248 |
| 94 | Me | Br | Br | H | H | 255-256 |
| 95 | Me | Br | Br | Me | H | 183-184 |
| 96 | Me | Br | Br | i-Pr | H | 235-236 |
| 97 | Me | Br | Br | Me | Me | 242-243 |

*See Index Table C for ¹H NMR data.

INDEX TABLE B

| Compound | R¹ | R² | R³ | R⁴ | R⁵ | R⁶ | R⁷ | m.p. (° C.) |
|---|---|---|---|---|---|---|---|---|
| 98 | Me | Br | Cl | Me | H | H | Cl | 145-146 |
| 99 | Me | Br | Cl | Et | H | H | Cl | 148-149 |
| 100 | Me | Br | Cl | i-Pr | H | H | Cl | 174-175 |
| 101 | Me | Cl | Cl | Et | H | H | Cl | 167-168 |
| 102 | Me | Cl | Cl | i-Pr | H | H | Cl | 189-190 |
| 103 | Me | Cl | Cl | Me | H | H | Cl | 185-186 |
| 104 | Me | Br | Cl | Me | H | F | H | 152-153 |
| 105 | Me | Br | Cl | i-Pr | H | F | H | 134-136 |
| 106 | Me | Cl | F | H | H | H | F | 212-213 |
| 107 | Me | Cl | F | Me | H | H | F | 214-215 |
| 108 | Me | Br | F | H | H | H | F | 204-205 |
| 109 | Me | Br | F | Me | H | H | F | 222-223 |
| 110 | Me | Br | F | Et | H | H | F | 200-201 |
| 111 | Me | Br | F | i-Pr | H | H | F | 203-204 |
| 112 | Me | Cl | F | Et | H | H | F | 195-196 |

INDEX TABLE C

| Cmpd No. | ¹H NMR Data (CDCl₃ solution unless indicated otherwise) |
|---|---|
| 3 | (CDCl₃) 10.55 (s, 1H), 8.45 (d, 1H), 7.85 (dd, 1H), 7.55 (s, 2H), 7.40 (dd, 1H), 6.97 (s, 1H), 6.30 (b q, 1H), 2.98 (d, 3H), 2.24 (s, 3H) |
| 5 | (CDCl₃) 10.55 (s, 1H), 8.45 (d, 1H), 7.85 (dd, 1H), 7.57 (m, 2H), 7.37 (dd, 1H), 7.05 (s, 1H), 6.30 (b q, 1H) 2.98 (d, 3H), 2.24 (s, 3H) |
| 18 | (CDCl₃) 10.10 (br s, 1H), 8.38 (d, 1H), 7.75 (s, 1H), 7.65 (s, 1H), 7.60 (m, 1H), 7.34 (m, 1H), 7.10 (s, 1H), 6.58 (b q, 1H) 2.96 (s, 3H) |
| 24 | (CDCl₃) 10.12 (s, 1H), 8.56 (d, 1H), 7.85 (d, 1H), 7.58 (m, 2H), 7.40 (dd, 1H), 6.97 (s, 1H), 6.00 (b d, 1H) 4.22 (m, 1H), 2.25 (s, 3H), 1.26 (d, 6H) |
| 25 | (CDCl₃) 10.60 (s, 1H), 8.47 (d, 1H), 7.85 (dd, 1H), 7.56 (s, 2H), 7.39 (dd, 1H), 7.06 (s, 1H), 6.04 (b d, 1H) 4.20 (m, 1H), 2.24 (s, 3H), 1.26 (s, 6H) |
| 33 | (CDCl₃) 10.60 (s, 1H), 8.45 (d, 1H), 7.85 (d, 1H), 7.58 (s, 2H), 7.39 (m, 1H), 6.97 (s, 1H), 6.20 (b t, 1H) 3.46 (m, 2H), 2.25 (s, 3H), 1.25 (t, 3H) |
| 35 | (CDCl₃) 10.60 (s, 1H), 8.46 (d, 1H), 7.85 (d, 1H), 7.57 (s, 2H), 7.38 (m, 1H), 7.05 (s, 1H), 6.25 (b t, 1H) 3.46 (m, 2H), 2.24 (s, 3H), 1.25 (t, 3H) |
| 41 | (CDCl₃) 10.40 (s, 1H), 8.47 (d, 1H), 7.85 (d, 1H), 7.50 (s, 2H), 7.37 (dd, 1H), 6.63 (s, 1H), 5.97 (s, 1H) 4.68 (q, 2H), 1.42 (s, 9H) |

Biological Examples of the Invention

Test A

For evaluating control of diamondback moth (*Plutella xylostella*) the test unit consisted of a small open container with a 12-14-day-old radish plant inside. This was pre-infested with 10-45 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc. Greeley, Colo., USA). The formulated compounds were applied in 1 mL of liquid through a SUJ2 atomizer nozzle with ⅛ JJ custom body (Spraying Systems Co. Wheaton, USA) positioned 1.27 cm (0.5 inches) above the top of each test unit. All experimental compounds in these tests were sprayed at 50 ppm replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed based on foliage consumed.

Of the compounds tested the following provided very good to excellent levels of plant protection (20% or less feeding damage): 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 63, 64, 65, 66, 67, 68, 69, 70, 71, 72, 73, 74, 75, 76, 77, 78, 79, 80, 81, 82, 83, 84, 88, 89, 90, 91, 92, 94, 95, 96, 97, 98, 99, 100, 101, 102, 103, 106, 108, 109, 110, 111 and 112.

Test B

For evaluating control of fall armyworm (*Spodoptera frugiperda*) the test unit consisted of a small open container with a 4-5-day-old corn (maize) plant inside. This was pre-infested (using a core sampler) with 10-15 1-day-old larvae on a piece of insect diet.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (20% or less feeding damage): 1, 2, 3, 4, 5, 6, 7, 8, 9, 10, 11, 12, 13, 14, 15, 16, 17, 18, 20, 21, 22, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 63, 64, 65, 66, 67, 68, 70, 73, 74, 76, 78, 88, 91, 92, 94, 95, 96, 98, 99, 100, 101, 102, 103, 106, 109, 110, 111 and 112.

Test C

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The larvae moved onto the test plant as the leaf piece desiccated. After pre-infestation, the soil of the test unit was covered with a layer of sand.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.). The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in this screen were sprayed at 250 ppm, replicated three times. After spraying of the formulated test compound, each test unit was allowed to dry for 1 hour and then a black, screened cap was placed on top. The test units were held for 6 days in a growth chamber at 19-21° C. and 50-70% relative humidity. Each test unit was then visually assessed for insect mortality.

Of the compounds tested, the following resulted in at least 80% mortality: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 43, 44, 46, 47, 48, 49, 50, 51, 52, 53, 55, 56, 63, 65, 66, 67, 68, 69, 70, 73, 74, 76, 78, 88, 89, 90, 91, 92, 94, 95, 96, 98, 99, 100, 101, 102, 103, 106, 108, 109, 110, 111 and 112.

Test D

For evaluating control of potato leafhopper (*Empoasca fabae* Harris) through contact and/or systemic means, the test unit consisted of a small open container with a 5-6 day old Longio bean plant (primary leaves emerged) inside. White sand was added to the top of the soil and one of the primary leaves was excised prior to application. Test compounds were formulated and sprayed at 250 ppm and replicated three times as described for Test C. After spraying, the test units were allowed to dry for 1 hour before they were post-infested with 5 potato leafhoppers (18 to 21 day old adults). A black, screened cap was placed on the top of the cylinder. The test units were held for 6 days in a growth chamber at 19-21° C. and 50-70% relative humidity. Each test unit was then visually assessed for insect mortality.

Of the compounds tested, the following resulted in at least 80% mortality: 1, 3, 4, 5, 6, 8, 10, 12, 16, 17, 18, 19, 20, 21, 22, 23, 24, 25, 26, 27, 28, 29, 32, 33, 34, 35, 37, 38, 40, 41, 43, 44, 46, 47, 48, 49, 50, 51, 52, 53, 54, 55, 56, 63, 66, 67, 68, 70, 73, 76, 88, 89, 90, 94, 95, 98, 99, 101, 103, 106, 108, 109, 110, 111 and 112.

Test E

For evaluating control of cotton melon aphid (*Aphis gossypii*) through contact and/or systemic means, the test unit consisted of a small open container with a 6-7-day-old cotton plant inside. This was pro-infested with 30-40 insects on a piece of leaf according to the cut-leaf method described for Test C, and the soil of the test unit was covered with a layer of sand.

Test compounds were formulated and sprayed at 250 ppm as described for Test D. The applications were replicated three times. After spraying, the test units were maintained in a growth chamber and then visually rated as described for Test D.

Of the compounds tested, the following resulted in at least 80% mortality: 1, 2, 3, 4, 5, 6, 7, 8, 9, 10, 11, 12, 13, 14, 15, 16, 17, 18, 19, 20, 21, 22, 24, 25, 26, 27, 28, 29, 32, 33, 34, 35, 36, 37, 38, 39, 40, 41, 42, 43, 44, 46, 47, 48, 49, 50, 51, 52, 53, 55, 56, 63, 69, 71, 72, 74, 76, 78, 79, 81, 84, 88, 89, 90, 91, 92, 95, 96, 97, 98, 99, 100, 101, 102, 103, 106, 108, 109, 110, 111 and 112.

Test F

For evaluating control of corn planthopper (*Peregrinus maidis*) through contact and/or systemic means, the test unit consisted of a small open container with a 3-4 day old corn (maize) plant (spike) inside. White sand was added to the top of the soil prior to application. Test compounds were formulated and sprayed at 250 ppm and replicated three times as described for Test C. After spraying, the test units were allowed to dry for 1 hour before they were post-infested with 10-20 corn planthoppers (18- to 20-day old nymphs) by sprinkling them onto the sand with a salt shaker. A black, screened cap was placed on the top of the cylinder. The test emits were held for 6 days in a growth chamber at 19-21° C. and 50-70% relative humidity. Each test unit was then visually assessed for insect mortality.

Of the compounds tested, the following resulted in at least 80% mortality: 1, 2, 3, 4, 5, 6, 7, 8, 10, 11, 12, 13, 18, 20, 24, 25, 26, 27, 28, 29, 32, 33, 35, 37, 38, 39, 40, 41, 43, 45, 46, 47, 48, 49, 50, 51, 53, 56, 88, 89, 90, 91, 94, 95, 108 and 109.

Test G

For evaluating control of silverleaf whitefly (*Bemisia tabaci*), the test unit consisted of a 14-21-day-old cotton plant grown in Redi-earth® media (Scotts Co.) with at least two true leaves infested with 2nd and 3rd instar nymphs on the underside of the leaves.

Test compounds were formulated in no more than 2 mL of acetone and then diluted with water to 25-30 mL. The formulated compounds were applied using a flat fan air-assisted nozzle (Spraying Systems 122440) at 10 psi (69 kPa). Plants were sprayed to run-off on a turntable sprayer. All experimental compounds in this screen were sprayed at 250 ppm and replicated three times. After spraying of the test compound, the test units were held for 6 days in a growth chamber at 50-60% relative humidity and 28° C. daytime and 24° C. nighttime temperature. Then the leaves were removed and the dead and live nymphs were counted to calculate percent mortality.

Of the compounds tested, the following resulted in at least 80% mortality: 2, 3, 4, 5, 7, 8, 9, 10, 24, 25, 26, 27, 28, 30, 32, 33, 34, 35, 38, 41, 46, 48, 49, 51, 52, 53, 66, 67, 70, 73, 88, 92 and 98.

Test H

For evaluating movement of compounds in plants and control of green peach aphid (*Myzus persicae*) and potato leafhopper (*Empoasca fabae*) after foliar movement of compound through the plant, the test unit consisted of a small open container with a 12-15-day-old radish plant (for green peach aphid test) or 5-6 day old Longio bean plant (for potato leafhopper test).

Test compounds were formulated using a solution containing 10% acetone, 90% water and 600 ppm X-770 Spreader Lo-Foam Formula non-ionic surfactant containing alkylarylpolyoxyethylene, free fatty acids, glycols and isopropanol (Loveland Industries, Inc.). The formulated compounds were applied in 20 microliters by pipet to two larger photosynthetically active leaves. All experimental compounds in this screen were applied at 1000 ppm, and the tests were replicated three times. After applying the formulated test compounds, the soil of each test unit was covered with a layer of sand and each test unit was allowed to dry for 1 hr and then a black, screened cap was placed on top. The test units were held in a growth chamber at about 20° C. and 50-70% relative humidity.

After 2 days, the treated leaves were covered on all sides with a fine plastic mesh, but with the leaf petiole intact and still attached to the plant to allow normal vascular movement and photosynthesis. The plants were then infested with 20-30 aphids (radish) or 20 leafhoppers (bean) and held in the growth chamber for 8 additional days. Each test unit was then visually assessed for mortality of the insects, which had contacted and fed on the untreated plant tissues.

Results of green peach aphid mortality (% GPA M) and potato leafhopper mortality (% PLH are listed in Table A.

TABLE A

| | Percent Insect Mortality | |
|---|---|---|
| Compound | % PLH M | % GPA M |
| 1 | 58 | 87 |
| 3 | 96 | 81 |
| 4 | 93 | 78 |
| 5 | 96 | 94 |
| 6 | 77 | 100 |
| 26 | 73 | 67 |
| 27 | 13 | 57 |

Test I

For evaluating movement of compounds in plants and control of green peach aphid (*Myzus persicae*) and potato leafhopper (*Empoasca fabae*) after xylem movement of compound from soil application up through roots into foliage, the test unit consisted of a small open container with a 12-15-day-old radish plant (for green peach aphid test) or 5-6-day-old Longio bean plant (for potato leafhopper test).

Test compounds were formulated using a solution containing 10% acetone, 90% water and 600 ppm X-77® Spreader Lo-Foam Formula non-ionic surfactant containing alkylarylpolyoxyethylene, free fatty acids, glycols and isopropanol (Loveland Industries, Inc.). The formulated compounds were applied in 1 mL of solution by pipet to the soil at the base of the plant. All experimental compounds in this screen were applied at 1000 ppm, and the tests were replicated three times. After applying the formulated test compounds, each test unit was allowed to dry for 1 h. The soil of each test unit was covered with a layer of sand and then a black, screened cap was placed on top. The test units were held in a growth chamber at about 20° C. and 50-70% relative humidity.

After 2 days, the plants were then infested with 20-30 aphids (radish) or 20 leafhoppers (bean) and held in the growth chamber for 5 additional days. Each test unit was then visually assessed for mortality of the insects, which had contacted and fed on the untreated plant foliage.

Results of green peach aphid mortality (% GPA M) and potato leafhopper mortality (% PLH M) are listed in Table B.

TABLE B

| | Percent Insect Mortality | |
|---|---|---|
| Compound | % PLH M | % GPA M |
| 1 | 100 | 64 |
| 2 | 56 | 64 |
| 5 | 95 | 40 |
| 6 | 100 | 59 |

What is claimed is:

1. A method for controlling an invertebrate pest of the order of Lepidoptera or Homoptera, comprising contacting the invertebrate pest or its environment with a biologically effective amount of a compound of Formula 1, an N-oxide or a salt thereof

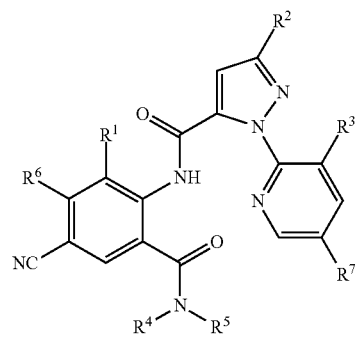

wherein:
R$^1$ is Me, Cl, Br or F;
R$^2$ is F, Cl, Br or C$_1$-C$_4$ haloalkoxy;
R$^3$ is F, Cl or Br;
R$^4$ is H; C$_1$-C$_4$ alkyl, C$_3$-C$_4$ alkenyl, C$_3$-C$_4$ alkynyl, C$_3$-C$_5$ cycloalkyl, or C$_4$-C$_6$ cycloalkylalkyl, each optionally substituted with one substituent selected from the group consisting of halogen, CN, SMe, S(O)Me, S(O)$_2$Me, and OMe;
R$^5$ is H or Me;
R$^6$ is H, F or Cl; and
R$^7$ is H, F or Cl.

2. A method for controlling an invertebrate pest of the order of Lepidoptera or Homoptera, comprising contacting the invertebrate pest or its environment with a biologically effective amount of a composition comprising a compound of Formula 1, an N-oxide or a salt thereof

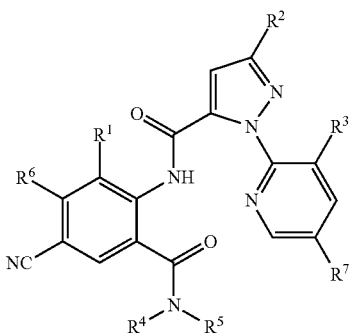

wherein:
R¹ is Me, Cl, Br or F;
R² is F, Cl, Br or $C_1$-$C_4$ haloalkoxy;
R³ is F, Cl or Br;
R⁴ is H; $C_1$-$C_4$ alkyl, $C_3$-$C_4$ alkenyl, $C_3$-$C_4$ alkynyl, $C_3$-$C_5$ cycloalkyl, or $C_4$-$C_6$ cycloalkylalkyl, each optionally substituted with one substituent selected from the group consisting of halogen, CN, SMe, S(O)Me, S(O)₂Me, and OMe;
R⁵ is H or Me;
R⁶ is H, F or Cl; and
R⁷ is H, F or Cl;
and at least one additional component selected from the group consisting of a surfactant, a solid diluent and a liquid diluent;
provided that the method is other than a soil drench.

3. The method of claim 1 wherein the compound of Formula 1 is 3-bromo-1-(3-chloro-2-pyridinyl)-N-[4-cyano-2-methyl-6-[(methylamino)carbonyl]phenyl]-1-pyrazole-5-carboxamide.

4. The method of claim 2 wherein the compound of Formula 1 is 3-bromo-1-(3-chloro-2-pyridinyl)-N-[4-cyano-2-methyl-6-[(methylamino)carbonyl]phenyl]-1-pyrazole-5-carboxamide.

5. The method of claim 2 wherein the surfactant is selected from the group consisting of polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers.

6. The method of claim 5 wherein the surfactant is a polyoxypropylene/polyoxyethylene block copolymer.

* * * * *